(12) United States Patent
Usui

(10) Patent No.: US 6,264,681 B1
(45) Date of Patent: Jul. 24, 2001

(54) FOOT WARMING EXOTHERMIC DEVICE

(75) Inventor: Akio Usui, Tochigi (JP)

(73) Assignee: Kabushiki Kaisha Genchi Kenkyusho, Tochigi Pref (JP)

( * ) Notice: Subject to any disclaimer, the term of this patent is extended or adjusted under 35 U.S.C. 154(b) by 0 days.

(21) Appl. No.: 09/371,957

(22) Filed: Aug. 11, 1999

Related U.S. Application Data

(63) Continuation-in-part of application No. 08/827,760, filed on Apr. 10, 1997, now abandoned.

(30) Foreign Application Priority Data

Apr. 11, 1996 (JP) .................................................. 8-115312

(51) Int. Cl.⁷ .................................................. A61F 7/00
(52) U.S. Cl. .......................... 607/111; 607/114; 607/108
(58) Field of Search .................................... 607/111, 114, 607/96, 108

(56) References Cited

U.S. PATENT DOCUMENTS

| | | | |
|---|---|---|---|
| Re. 32,026 | * 11/1985 | Yamashita et al. ................... | 126/263 |
| 4,516,564 | * 5/1985 | Koiso et al. ........................... | 126/263 |
| 4,756,299 | * 7/1988 | Podella .................................. | 126/263 |
| 4,925,743 | * 5/1990 | Ikeda et al. ........................... | 428/702 |
| 5,046,479 | * 9/1991 | Usui ...................................... | 126/204 |
| 5,184,613 | * 2/1993 | Mintz ..................................... | 128/402 |
| 5,230,333 | * 7/1993 | Yates et al. ........................... | 128/382 |
| 5,233,981 | * 8/1993 | Miyashita ............................... | 607/114 |
| 5,331,688 | * 7/1994 | Kiyohara .................................. | 2/239 |
| 5,342,412 | * 8/1994 | Ueki ....................................... | 607/114 |
| 6,099,556 | * 8/2000 | Usui ....................................... | 607/114 |

* cited by examiner

*Primary Examiner*—Linda C. M. Dvorak
*Assistant Examiner*—Jocelyn Ram
(74) *Attorney, Agent, or Firm*—Ronald E. Greigg; Edwin E. Gregg

(57) ABSTRACT

A method of manufacturing a foot warming exothermic device comprises placing an exothermic composition of a viscous fluid form by printing or coating on one surface of a thin sheet base material and in at least one predetermined portion of the one surface to such a configuration as to cover a desired site of a human foot, and then placing a thin sheet covering material on the fluid exothermic composition so as to cover the exothermic composition, at least one or part of the base material and the covering material being gas permeable.

6 Claims, 8 Drawing Sheets

FOOT WARMING EXOTHERMIC DEVICE

This application is a continuation-in-part of application (s) application Ser. No. 08/827,760 field on Apr. 10, 1997 now abandoned.

BACKGROUND OF THE INVENTION

(1) Field of the Invention

The present invention relates to a method of manufacturing a foot warming exothermic device and the foot warming exothermic device. More particularly, the invention relates to a method of manufacturing a foot warming exothermic device which can easily produce an ultrathin foot warming exothermic device at low cost by placing a fluid exothermic composition on a wrapper at high speed, can securely fix a portion or the whole of the exothermic composition in the wrapper and prevent movement thereof, and can well conform to the user's foot configuration and efficiently warm a desired site of the foot when it is applied to the site, and to the foot warming exothermic device.

(2) Description of the Related Art

In recent years, exothermic devices of the type known as disposable body warmers have been widely used such that the exothermic device includes an exothermic composition enclosed in a flat pouch comprised of a gas permeable or gas-tight thin sheet base material and a gas permeable thin sheet covering material.

It is also common to use an exothermic device having an adhesive layer attached to one side of a pouch of the above noted type such that the exothermic device can be pasted directly or through underwear to the skin of a living body. Further, it has been proposed to utilize as a hot compress an adhesive layer with a wet pack medication incorporated or carried therein, or as a medication-containing layer with a skin absorbable medication incorporated or carried therein (see Japanese Patent Application published specification No. 2-149272).

As an old saying goes, "cooled head and warmed feet", it has been believed that warming feet is a key to good health. With widespread use of such exothermic devices, therefore, foot warming exothermic devices for warming the sole of the foot have now become commercially available. Various foot warming exothermic devices of this type have been proposed including, for example, those disclosed in Japanese Patent Application published specifications Nos. 2-154762, 2-172460, 5-115310, Japanese Utility Model Applications published Nos. 6-21616 and 5-84317, and Japanese Patent Application published No. 5-176951.

In manufacturing such a foot warming endothermic device it is general practice to place an exothermic composition of powder form with some water content on a predetermined site in a base material and then cover the same with a gas permeable covering material. Thereafter, the base material and a peripheral edge portion of the covering material are sealingly bonded by heat sealing or with a hot melt adhesive over and along the entire peripheral edge portion.

Such a foot warming exothermic device of the prior art includes an exothermic composition containing, in traditionally appropriate proportions, a metal powder, such as iron powder, and water, and in addition an activated carbon for accelerating heat generation, a metal chloride for fracturing an oxide film on the surface of the metal powder and continuously generating an exothermic reaction,and a water retainer for preventing a sticky effect of the composition. The exothermic composition is in the form of a water-containing powder and is placed on a base material.

In the case where the exothermic composition, with all its ingredients mixed together in an appropriate blend ratio as above noted, is placed on the base material, the trouble is that after the blending of the ingredients into the exothermic composition and before the foot warming exothermic device is enclosed in an outer pouch, an exothermic reaction occurs which results in a loss of exothermic energy and a quality degradation of the exothermic composition. Furthermore, a reaction product resulting from the exothermic reaction involves various harmful effects, such as decreased yield, handling inconvenience, complicated maintenance-related problems, limitations affecting machine operation time as well as operator working hours, and difficulties involved in dealing with coagulated matter.

While the exothermic composition is provided through its water content with a wetting characteristic, the proportion of the water content is so low as to be suitable for an exothermic reaction, so that the exothermic composition assumes a powder form and has only poor fluidity. This poses a problem that it is extremely difficult to allow the composition to be uniformly distributed within a predetermined area on the base material through mere placement of the same in position. In view of this fact, it is common practice to equalize the distribution of the exothermic composition to some extent by means of a roller or the like during the process of covering the composition with a covering material and sealing the same. With such a method, however, the distribution of the exothermic composition tends to become inclined toward the source of pouch material. In order to increase the proportion of the exothermic composition distributed in the direction of pouch material feed, it is necessary to increase the height of a chamber defined within the pouch, thereby making it possible to eliminate any offset in the distribution of the exothermic composition as by manual shaking at the time of use.

Where the foot warming exothermic device becomes thicker in its entirety, the device feels rough and has poor hand. Moreover, the device has inferior flexibility so that it is unable to well conform to any complex surface irregularity at an application site and/or any curved surface of a small curvature. The thickness increase also results in a degradation in the extensibility or stretchability characteristic of the device, which in turn may result in a deformation due to the wearer's movement and a lower capability of conformance to such movement.

Furthermore, as already mentioned, foot warming exothermic devices of the prior art are such that although the exothermic composition is provided through its water content with wetting characteristics, the proportion of the water content is so low as to be suitable for an exothermic reaction, so that the exothermic composition assumes a powder form and has only poor fluidity. Therefore, it is extremely difficult to cause the exothermic composition to be uniformly distributed within a predetermined area on the base material, so that the thickness of the foot warming exothermic device is irregular. As such, when the device is used in such a condition that it is affixed to an application site, continued use of the device as affixed to the same application site may be a cause of a low temperature burn.

With foot warming exothermic devices of the prior art, it is impossible to completely prevent any possible displacement during the process of manufacture or in the course of transportation in the current status of the art.

Such foot warming exothermic device, prior to use, is transported for delivery in a condition such that it is packaged within an outer pouch (preservation pouch). In this stage of transport, the exothermic composition is movable within the exothermic device and, from the standpoint of safety maintenance, it has been taken as an important requirement that the device be kept uniform in thickness so as to enable the device to exhibit a constant temperature profile throughout its entirety. In the current practice, therefore, any such device in which the exothermic composition is non-uniformly distributed is returned as an off-standard product in the stage of distribution, or is replaced upon request from the user. Hence, it is very important to secure thickness uniformity with respect to the exothermic composition in the stage of transportation.

In Japanese Patent Application Laid-Open No. 62-347, a method for adhesively fixing an exothermic composition in position is proposed. In actual manufacturing operation, however, it is almost impossible to adhesively fix an exothermic composition in powder form within a pouch. Even if such adhesion could be done, the adhesion would be too weak to enable the composition to be well fixed in position, and therefore the composition, while in use, may become peeled off or may become a plate-like mass having little flexibility, thus causing an uncomfortable feeling to the user. Furthermore, the presence of the adhesive hinders contact of the composition with air, resulting in an uneven temperature distribution and/or temperature variations. As such, this method is unsatisfactory for practical use.

Therefore, the inventor has made intensive research in order to solve the above-mentioned technical problems thereby to develop a method of manufacturing a foot warming exothermic device which can inhibit any exothermic reaction of an exothermic composition and prevent any possible heat loss due to heat generation during a manufacturing operation and various harmful effects of quality degradation and solidification of the exothermic composition, and can manufacture ultra-thin exothermic devices at a high rate, and which permits the exothermic composition to be uniformly distributed and fixed within a pouch thereby to prevent any movement and/or displacement of the exothermic composition and suppress an excessive exothermic reaction of the composition.

It has been found as a result that the heating principle of an exothermic device of this type is based on a heat generation occurring with the oxidation of a metal powder, and the rate of this oxidation, or exothermic reaction, is greatly influenced by the quantity of water in particular.

That is, to promote this oxidation, an appropriate 10 degree of moisture is the key, the reaction is markedly retarded if moisture is too much or too little. A good balance between necessary moisture and air (oxygen) supply is said to maximize the rate of oxidation or exothermic reaction.

Too little moisture results in a shortage of moisture necessary for the reaction though air is sufficient. Too much moisture results in barrier layers of moisture to diminish air supply, thereby retarding the reaction.

The inventor has found that use of a fluid exothermic composition, that is, an exothermic composition made viscous, makes it possible to manufacture an ultra-thin exothermic device at a high rate of production because the composition can be easily transferred by printing, e.g., screen printing, or coating, and that since any excess moisture forms barrier layers of moisture to diminish air supply thereby to substantially stop any exothermic reaction in progress, any quality degradation of the exothermic composition in process and various harmful effects of the solidification of the composition can be prevented.

The inventor has also found that by causing an exothermic composition to be formed into a viscous fluid configuration, the exothermic composition can be uniformly distributed within a pouch by printing, e.g., screen printing, or coating, and that when the fluid exothermic composition is transferred or laminated on a water-absorbable foamed film sheet, paper, corrugated board, cardboard core paper, nonwoven cloth, woven cloth, or porous thin sheet, or on a water absorptive layer formed on such material, the fluid exothermic composition can be fixed in position on such foamed thin sheet, nonwoven cloth, woven cloth, or porous thin sheet, or on the water absorptive layer formed thereon, being thereby prevented from movement.

Further, the inventor has found that use of a printing technique, such as screen printing, or a lamination technique, such as coating, enables the formation of the exothermic device to a very thin configuration, which results in a decrease in the rate of exothermic reaction per unit time, whereby an excessive exothermic reaction of the exothermic composition can be suppressed. Additionally, the inventor has found that where a fluid exothermic composition is laminated on a Wrapper material, e.g., paper, card board, card board core, or nonwoven cloth, such as of rayon, by using a printing technique, such as screen printing, or a coating technique, the stage of powder inputting can be eliminated in the process for manufacturing an exothermic device, which simplifies the process of factory management which must be carried out to the satisfaction of the GMP standards in the manufacture of medical tools and devices and medicament supplies in the future.

Further, the inventor has found that when part of the moisture content of a fluid exothermic composition in which the proportion of water is relatively high is absorbed into a wrapper material, such a base material and/or covering material, barrier layers go out of existence, whereby any possible harmful effect of excessive moisture can be eliminated.

Further, the inventor has found that a fluid exothermic composition acts to adhesively join the base material and the covering material together and bites into rough surfaces of the base material and the covering material and, therefore, that through such anchoring effect of the exothermic composition, any possible displacement of the composition within the exothermic device can be prevented not only in the manufacturing process, but also in the stage of distribution and during use by the consumer.

Conventional foot warming exothermic devices have a drawback that heat generation cannot completely be controlled. In some cases, an abrupt temperature rise (to about 90° C.) may occur when the user puts off his shoes, with the result that the duration of heating becomes extremely short. Depending upon the type of shoes and/or individual physical constitution, such devices often involve problems of insufficient heat generation and burn due to excessive heating. There are many who suffer from foot cold and a great need exists for a safe foot warming exothermic device.

The temperature of the foot sole is associated with blood stream and is influenced by changes in ambient temperature, such as atmospheric temperature, in delicately varied degrees, depending upon sole temperature changes during morning, day time, and night time, changes in physical condition, meals, and the quantity of exercise. Of course, this is not the same with all people, there being considerable difference among individuals.

Further, there are many factors affecting heat generation, including type of shoes, type of socks, whether the shoe is tight or loose, and in condition of heat insulation. Even if the conditions for heat generation are kept constant, where the conditions are favorable for heat generation, there may be a danger of excessive heating, which means a danger of burn. Whilst, where the conditions are unfavorable for heat generation, there may be unsatisfactory heat generation, thus the device is rendered useless.

In contrast to conventional foot warming exothermic devices, with respect to a foot warming exothermic device having an exothermic composition incorporated therein by transfer, it has been found that even if the proportion of iron powder, a heat generating material, is increased to 60% in weight ratio to the total of all ingredients, air barrier layers (moisture-containing layers) in a fluid which cover the iron powder or heat generating material can become air permeable as moisture is deprived of them as a result of an exothermic reaction of the iron powder since the transfer of the exothermic composition is effected by using a thickener. Furthermore, air supply can be gradually obtained through the surface of the device. Thus, a stable heat generation can be obtained, and if conditions for heat generation are changed, still a favorable heat generation can be obtained.

SUMMARY OF THE INVENTION

The present invention has been developed on the basis of the foregoing findings, and accordingly it is an object of the invention to provide a method of manufacturing a foot warming exothermic device and the foot warming exothermic device which inhibit an exothermic reaction of an exothermic composition and prevent any possible heat loss due to heat generation during a manufacturing operation and various harmful effects of quality degradation and solidification of the exothermic composition; which enable uniform distribution of the exothermic composition through the utilization of a transfer/lamination technique, such as printing, e.g., screen printing, or coating, and can enhance lamination reliability thereby to stabilize product quality, thus enabling manufacture of ultra-thin exothermic devices in a simple way and at a high rate; which enable the fluid exothermic composition to be uniformly distributed and immobilized within a pouch by laminating the exothermic composition on a water-absorbable foamed thin sheet, paper, corrugated board, cardboard core paper, nonwoven fabric of rayon, for example, woven cloth, or a porous thin sheet, or on a water absorptive layer formed on such material, whereby the exothermic composition can be prevented from movement and displacement; and which enables the fluid exothermic composition to be prevented from any excessive exothermic reaction as far as possible through thickness reduction with respect to the composition.

It is another object of the invention to provide a method of manufacturing a foot warming exothermic device and the foot warming exothermic device wherein a fluid exothermic composition is transferred onto a wrapper material, e.g., paper, card board, card board core or nonwoven cloth, such as of rayon, by using screen printing technique, so that the stage of powder transfer can be eliminated, which simplifies factory management requirements for meeting the GMP standards in the manufacture of medical tools and devices and pharmaceutical supplies in the future.

The inventor has found that by placing a fluid exothermic composition on a thin sheet base material, then placing a thin sheet covering material thereon, the base material and the covering material being bonded together through the utilization of the viscosity of the fluid exothermic composition, then cutting out the resulting laminate to such a shape as to cover a desired application site, it is also possible to produce an ultra-thin foot warming exothermic device such that the fluid exothermic composition is uniformly distributed and immobilized within a pouch and that any excessive exothermic reaction of the exothermic composition is prevented as far as practicable.

The present invention has been developed on the basis of the foregoing finding, and accordingly it is another object of the invention to provide a method of manufacturing a foot warming exothermic device and the foot warming exothermic device wherein the exothermic device is produced by placing a fluid exothermic composition on a thin sheet base material, then placing a thin sheet covering material thereon, at least one of the base material and the covering material being water absorptive or rendered water absorptive by a certain treatment, the base material and the covering material being bonded together through the utilization of the viscosity of the fluid exothermic composition, then cutting out the resulting laminate to such a shape as to cover a desired foot site whereby an exothermic reaction of the fluid exothermic composition is suppressed, and any possible heat loss due to heat generation during a manufacturing operation, quality degradation, and various harmful effects of solidification of the exothermic composition are prevented, and wherein the device can be produced in the form of an ultra-thin foot warming exothermic device such that the exothermic composition is prevented from movement and displacement and that any excessive exothermic reaction of the exothermic composition is prevented as far as possible. In order to accomplish the above objects, a first method of manufacturing a foot warming exothermic device in accordance with the present invention (hereinafter referred to as first method of the invention) comprises: placing an exothermic composition of a viscous fluid by printing or coating on one surface of a thin sheet base material and in at least one predetermined portion of said one surface to such a configuration as to cover an arbitrary site of a human foot, and then placing a thin sheet covering material on said exothermic composition so as to cover the exothermic composition, at least one or part of said base material and said covering material being gas permeable.

The first method of the invention will now be described in detail.

The first method of the invention is characterized in that the exothermic composition to be used is a fluid exothermic composition, and not of a powder form as in the prior art.

The exothermic composition is not particularly limited as long as it comprises a component which reacts with oxygen in the ambient air to produce an exothermic reaction and is able to flow when an external force is applied. That is, there is no particular limitation with respect to the composition as long as the composition can be transferred and/or laminated by printing, such as screen printing, or coating. Such a fluid exothermic composition can be obtained by regulating the mixing ratio of necessary components, that is, the ratios of water, a water absorptive polymer and/or a thickener to other components.

In the first method of the invention, the use of such fluid exothermic composition, as the exothermic composition, in particular provides various advantages as stated below.

That is, in the first method of the invention, the use of the fluid exothermic composition much simplifies the process of lamination by printing, such as screen printing, or coating, and enables a high-speed production of an ultra-thin foot warming exothermic device. Further, the method enables a uniform distribution of the exothermic composition within a pouch. In addition, when the exothermic composition is laminated on a foamed thin sheet, paper, nonwoven fabric of rayon or the like, woven cloth, or on a porous thin sheet, the exothermic composition exhibits a high anchoring characteristic so that it bites into pores of the thin sheet, which prevents movement and/or displacement of the composition.

In this case, where such a film or sheet has a water absorptive ability and the exothermic composition is laminated on the film or sheet, or where a water absorptive layer is formed on the thin sheet and the exothermic composition is laminated on the water absorptive layer, the whole or part of the exothermic composition can be more easily secured to the foamed thin sheet, paper, nonwoven cloth, woven cloth, or porous thin sheet, or to the water absorptive layer formed thereon, with the result that the composition can be prevented more positively from movement or displacement.

The use of a lamination technique by way of printing, such as screen printing, or coating enables production of a very thin exothermic device. In contrast to prior art exothermic compositions in powder form, the exothermic composition has an area limited for contact with air so that the quantity of its heat generation per unit time is limited. Thus, an excessive exothermic reaction of the exothermic composition is suppressed. Further, because of the fact that the exothermic composition is in the form of a fluid and has a thin layer thickness, any movement and/or displacement of the exothermic composition itself can be inhibited.

Furthermore, according to the first method of the invention, where the exothermic composition is transfer-laminated by printing, such as screen printing, or coating on a water-absorptive wrapper material, such as foamed thin sheet, paper, card board, card board core material, nonwoven fabric of rayon or the like, woven cloth, or porous thin sheet, the step of powder inputting is eliminated, and this simplifies the process of plant management to meet the GPM standards in the manufacture of medical tools and medicaments in the future.

In the first method of the invention, the use of the fluid exothermic composition provides various advantages as mentioned above. Particularly where, in the preparation of the exothermic composition, the proportion of water in the exothermic composition is arranged to be higher and, in addition, a water absorptive polymer and/or a thickener is mixed into the composition for adjustment to enable the composition to be formed into a viscous exothermic composition, the process of transfer/lamination by printing or coating can be performed very easily and a high-rate production of an ultra-thin exothermic device can be achieved. Further, free water or excess water forms barrier layers to diminish the supply of air, with the result that exothermic reaction is substantially stopped. This is desirable because various harmful effects which may otherwise arise from an exothermic loss during the process of manufacture, quality degradation of the exothermic composition, and coagulation of the exothermic composition can be prevented.

In the prior art exothermic compositions, the proportion of water is only adequate to allow an exothermic reaction and there is no moisture-based barrier layer formed on the surface of the metal powder, more particularly on the surface of iron powder, and therefore an exothermic reaction progresses smoothly and continuously through a contact of the composition with air. As such, an exothermic reaction occurs after the composition is loaded and before an exothermic device manufactured as such is enclosed in an outer pouch, there arises a loss due to the exothermic reaction which results in a quality degradation of the exothermic composition. In addition, masses produced by the exothermic reaction coagulate to present various troubles, such as reduced yield, handling difficulty, troublesome additional jobs affecting plant maintenance operation, inconveniences caused in relation to plant operation time and/or operator's working hours, and inconvenient work involved in coagulated mass treatment.

In the first method of the invention, there is no particular limitation with respect to the method for depositing a viscous exothermic composition on the base material. Preferably, however, the composition be deposited by using known printing techniques, for example, thick-film printing, gravure printing, offset printing, screen printing, or spraying, or by coating or transferring by means of a head coater, a roller, and/or an applicator.

Any conventional exothermic composition has a wetting characteristic given through its water content, but the proportion of the water therein is only adequate to enable thermal reactions. Therefore, the composition has only poor fluidity, which makes it extremely difficult to allow the composition to be uniformly distributed within a predetermined area on the base material by a mere throw-down placement.

In contrast, according to the first method of the invention, a thickener is added to the exothermic composition in preparing the exothermic composition so that the composition has a viscous characteristic. The exothermic composition can be easily transferred by printing, such as screen printing, or coating, and enables a high-rate production of the ultra-thin exothermic device. Furthermore, any free moisture and excess water present forms barrier layers to diminish the quantity of air supply, so that there is almost no possibility of an exothermic reaction being allowed to occur.

Where the proportion of water is relatively high in the exothermic composition so that the free moisture and excess water present therein form barrier layers, part of the water content of the exothermic composition may be absorbed by the base material and/or a wrapper material, such as a covering material, or by a water absorptive layer formed on the base material and/or the covering material. Then, the barrier layers will go out of existence and any inconvenience due to excessive water can be eliminated.

In the first method of the invention, the exothermic composition which constitutes the exothermic composition comprises, as essential ingredients thereof, water, a water absorptive polymer, a thickener, and other materials, that is, materials other than those essential for exothermic reaction, including a carbon component, such as carbon or activated charcoal, for promoting heat generation, and a metal chloride for fracturing an oxide film on the surface of a metal powder and continuously generating an exothermic reaction. Where so desired, an inorganic or organic water retainer, a pH adjustor, a surface active agent for dispersability enhancement, and/or an anti-foaming agent may be compounded into the composition. Thus, the exothermic composition, in its entirety, is in the form of a fluid.

The proportions of various ingredients of the exothermic composition may vary depending upon the type of the water absorptive polymer, the types of the exothermic materials and carbon component, and the type of the metal chloride, but generally it is desirable that the water absorptive polymer be within the range of from 0.05 to 7.5 parts by weight relative to 100 parts by weight of the exothermic materials, the thickener from 0.05 to 10 parts by weight, carbon component from 1.5 to 20 parts by weight, and the metal chloride from 1 to 10 parts by weight. In the first method of the invention, water is added to a mixture of the above ingredients so that the entire mixture is rendered pasty. In this case, a predetermined amount of the metal chloride may be dissolved or dispersed in water, the resulting solution or dispersion being added to a mixture of the water absorptive polymer, thickener and carbon component to provide a composition in the form of paste as a whole.

In the first method of the invention, the exothermic composition, prepared in the form of a fluid as stated above, generally has a viscosity range (at 20° C.) of preferably from 50,000 to 6,500,000 cps as measured according to a method described hereinafter.

If the viscosity of the fluid exothermic composition is too low or less than 50,000 cps, the exothermic composition has poor transferability by printing or coating, an excessive water content which results in a shortage of transfer of other ingredients and a reduced duration of heat generation. Further, the low degree of viscosity results in a separation of the metal powder such as iron powder which makes it difficult to maintain the uniformity of the ingredients, and oozing of part of the fluid exothermic composition out of the predetermined site on the base material. In addition, such a low degree of viscosity may necessitate a large amount of moisture to be absorbed by the base material and/or the covering material after the process of transfer operation, the use of a base material and/or covering material of a special construction, and a complicated structure design for the exothermic composition. If the viscosity is more than 6,500,000 cps, the transferability of the composition is adversely affected, resulting in varied quantities of transfer and generation of exothermic reaction on the surface.

The viscosity herein means a value measured as such at a temperature of 20° C. by using a viscometer (Model BH) made by TOKIMEC INC., with a #7 rotor run at a rotational speed of 2 rpm, and using in conjunction therewith a beaker having an inner diameter of 85 ømm.

In the first method of the invention, where the fluid exothermic composition, as described above, comprises water, a water absorptive polymer, a thickener, and other materials including an exothermic material, a carbon component and a metal chloride, the composition exhibits the desired heat generating characteristic. However, where it is desired to achieve further improved temperature stability and further improvement in the duration of heat generation, an inorganic or organic water retainer, a pH adjustor, a surface active agent for dispersibility enhancement, and/or an anti-foaming agent can be advantageously loaded into the composition to produce a useful exothermic composition in a fluid form as a whole.

That is, it is preferable to use the water absorptive polymer within the range of from 0.05 to 7.5 parts by weight, the thickener from 0.05 to 10 parts by weight, the carbon component from 1.5 to 20 parts by weight, the metal chloride from 1 to 10 parts by weight, the inorganic or organic water retainer from 0.5 to 10 parts by weight, the pH adjustor from 0.1 to 5 parts by weight, the surface active agent for dispersibility enhancement from 0.1 to 5 parts by weight, and the defoaming agent from 0.1 to 5 parts by weight, relative to 100 parts by weight of the heat generating materials. In the first method of the invention, the mixture in particular is added with water so that the resulting composition in its entirety is in the form of a fluid. In this case, the metal chloride may be dissolved or dispersed in a predetermined quantity of water, the resulting solution or dispersion being added into a mixture consisting of the water absorptive polymer, the thickener, the carbon component, the inorganic or organic water retainer, the Ph adjustor, the surface active agent, and the defoaming agent, whereby the mixture as a whole is rendered pasty in its form.

In this case, too, as above stated, generally, the viscosity of the exothermic composition is preferably within the range (at 20° C.) of from 50,000 to 6,500,000 cps as measured according to the above described method.

Water absorptive polymers useful in the first method of the invention are typically polymeric materials which can absorb water and/or an aqueous solution of a metal chloride smoothly and in a large amount, specifically, for the water absorptive polymer is used one kind of material or a mixture of two or more kinds of materials as selected, for example, from the group consisting of starch- polyacrylonitrile copolymers disclosed in Japanese Patent Publication No. 49-43395, cross-linked polyalkylene oxides disclosed in Japanese Patent Publication No. 51-39672, vinyl ester-ethylene unsaturated carboxylic acid copolymer saponification products, self-crosslinked polyacrylates as produced by a reversed phase suspension polymerization method disclosed in Japanese Patent Publication No. 54-30710, reaction products of a polyvinyl alcohol polymer and a cyclic anhydride as disclosed in Japanese -Patent Application Laid-Open No. 54-20093, cross-linked polyacrylates disclosed in Japanese Patent Application Laid-Open No. 59-84305, and a cross-linked N-vinyl acetamide (water absorptive agent manufactured by Show a Denko K. K.; trade name: NA-Ob). These materials may be treated with or used in combination with a surface active agent for improvement of their hydrophilic characteristic. Some of these water absorptive polymers can absorb water and/or an aqueous solution of chloride to provide a thickening effect, but their main function is to absorb water and/or an aqueous metal chloride liquid smoothly and in a large amount.

For the water absorptive polymer, commercially available polymers of the kind may be used including, for example, products of Sanyo Kasei K. K., such as Sanwet IM-300, Sanwet IM-300MPS, Sanwet IM-1000, Sanwet IM-300MS, and Sanwet IM-1000MPS; products of Seitetsu Kagaku K. K., such as Aquakeep 4S and Aquakeep 45H; products of Sumitomo Kagaku K. K., such as Sumikagel NP-1020, Sumikagel NP-1040, Sumikagel SP-520, and Sumikagel N-1040; products of Kurare K. K., such as KI GEL 201-K and KI GEL 201K-F2; and products of Arakawa Kagaku K. K., such as Arasoap 800 and Arasoap 800F.

Especially preferred of these commercially available water absorptive polymers are Sanwet IM-300 MPS and Sanwet IM-1000MPS manufactured by Sanyo Kasei K. K.; Sumikagel NP-1020 and Sumikagel NP-1040 manufactured by of Sumitomo Kagaku K. K.; KI Gel 201-K and KI Gel 201-F2 manufactured by Kurare K. K.; and Arasoap 800F. manufactured by Arakawa Kagaku K. K., all of these being capable of quick and high absorption of water and an aqueous metal chloride liquid.

Thickening agents useful in the first method of the invention are typically materials which can absorb water and/or an aqueous solution of a metal chloride thereby to enhance cone penetration or impart a thixotropic characteristic to the composition. Specifically, for the thickener is used one kind of material or a mixture of two or more kinds pf materials as selected, for example, from among polyacrylates, such as bentonite, stearate, and soda polyacrylate; alginates, such as gelatin, polyethylene oxide, polyvinyl alcohol, polyvinyl pyrrolidone, tragacanth gum, locust bean gum, gum guar, guam arabic, and soda alginate; starch-based water absorptive agents, such as pectin, carboxyvinyl polymer, dextrin, alpha starch, and processing starch; polysaccharide-based thickening agents, such as carrageen an and agar; cellulose derivative-based thickening agents, such as CMC, ethyl cellulose acetate, hydroxyethyl cellulose, methyl cellulose, and hydroxypropyl cellulose; acrylosulfonic acid-based polymeric materials (e.g., "CS-6H5", manufactured by Nippon Khokubai K. K.); and water-soluble cellulose esters and poly-N-vinyl acetoamides. These materials may be treated with or used in combination with a surface active agent for improvement of their hydrophilic characteristic. These water absorptive polymers can absorb water and/or an aqueous solution of metal chloride to enhance cone penetration and provide a thixotropic effect.

Specific examples of above mentioned water-soluble cellulose ethers are varieties of methyl cellulose produced by etherifying a cellulose with a methoxyl group (Metolose SMiS, Metolose SM25, Metolose 5M400, and Metolose SM4000, manufactured by Shin-Etsu Kagaku Kogyo K. K.); varieties of hydroxypropylmethyl cellulose produced by etherifying cellulose with a hydroxypropoxyl group (Metolose 60SH-50, Metolose 60SH-4000, Metolose 90SH-4000, Metolose 90SH-3000, and Metolose 90SH-100000), and varieties of hydroxymethyl cellulose produced by etherifying cellulose with a hydroxyethoxyl group (made by Shin-Etsu Chemical Co.; trade names "Metolose 60SH-50, Metolose 60SH-4000, Metolose 90SH-4000, Metolose 90SH-3000, and Metolose 90SH-100000, manufactured by Shin-Etsu Kagaku Kogyo K. K.).

When an aqueous solution of such a water-soluble cellulose ether is heated up to, for example, a predetermined temperature (thickening start temperature), the viscosity of the solution is lowered. When further heated to a higher temperature, the adsorbed moisture is released so that the solution gains an increase in its viscosity to go into the state of a gel (this phenomenon is hereinafter referred to as gelation). The liberated moisture forms barrier layers to diminish an exothermic reaction. Whilst, when the gel is cooled, it adsorbs moisture to return to its original state.

The thickening start temperature of a water-soluble cellulose ether is influenced by the type of the etherifying agent, the degree of substitution, the molecular weight of the cellulose, and where the cellulose ether is added in the form of a solution, by the concentration thereof, and where other additive is added, by the type of the additive and the amount of addition (concentration) and also by the rate of temperature rise and the rate of cooling. Therefore, when a water-soluble cellulose ether is used as a thickening agent, the type of an etherifying agent, the degree of substitution, the cellulose molecular weight, the concentration of the solution, and the type of other additive and the amount of addition (concentration) thereof, as well as the make-up of the exothermic composition and the intended amount of use thereof, are suitably selected to control the rate of temperature rise and the rate of cooling thereby to suitably select a maximum heat generation temperature.

In the case of a 2 wt % aqueous solution of 8 water-soluble cellulose ether (e.g., Metolose SM4000 manufactured by Shin-Etsu Kagaku Kogyo K. K.), for example, where no additive is involved, the thickening start temperature is 55° C., but when 5 wt % of sodium chloride (NaCl) or 5 wt % of sodium carbonate ($Na_2CO_3 \cdot 10H_2O$) is added, the thickening start temperature is 40° C. When the device is applied directly to a human body, the Metolose SM4000 releases an adsorbed moisture at not more than a safety temperature (43° C.) thereby to inhibit an exothermic reaction.

Where 5 wt % of $Al_2(SO_4) \cdot 18H_2O$ is added, the thickening start temperature of Metolose 5M4000 is still 45° C., and at this temperature, Metolose 5M4000 releases an adsorbed moisture around the metal powder to inhibit the exothermic reaction.

In the case of a 2 wt % aqueous solution of a water-soluble cellulose ether (e.g., Metolose 60SH-4000), for example, if there is no additive present therein, the thickening start temperature is 75° C., but when 5 wt % of sodium chloride (NaCl) is added, the thickening start temperature is 70° C., and When 5 wt % of sodium carbonate is added, the thickening start temperature is 45° C. At these temperatures, Metolose 60SH-4000 releases an adsorbed moisture around the metal powder to inhibit the exothermic reaction.

Where 5 wt % of $Al_2(SO_4) \cdot 18H_2O$ is added, the thickening start temperature of Metolose 60SH4000 is 50° C., and at this temperature, Metolose 60SH-4000 releases an adsorbed moisture to increase the amount of free water around the metal powder thereby to inhibit the exothermic reaction.

Additives useful for adjusting the thickening start temperature of the above mentioned thickener are, for example, above mentioned sodium chloride and sodium carbonate, inorganic matter, such as aluminum sulfate hydrates, a lower alcohol, such as ethanol, polyvalent alcohols, such as polyethylene glycol and glycerine, and above mentioned water absorptive polymers and thickening agents.

The poly-N-vinylacetoamide is a material obtained through radical polymerization of N-vinylacetoamide. There are two types, one having a straight-chain structure which is water-soluble, and the other having a cross-linked structure which is water-insoluble. An example of the water-insoluble poly-N-vinylacetoamide is a microgel which functions as a gelling agent through the difference in crosslink density. Specifically, for the poly-N-vinylacetoamide is used one kind of material or a mixture of two or more kinds of material as selected from among, for example, N-vinylacetoamide-sodium acrylate copolymer (GE-167, manufactured by Showa Denko K. K.), N-vinylacetoamide homopolymer (GE-191, manufactured by Showa Denko K. K.), and N-vinylacetoamide cross-linked material (microgel) (GX-205, manufactured by Showa Denko K. K.). These materials may be treated with or used in combination with a surface-active agent for improvement of their hydrophilic characteristic. These water absorptive polymers can absorb water and/or an aqueous solution of metal chloride to enhance cone penetration and provide a thixotropic effect.

Of course, the water absorptive polymer and the thickener cannot strictly be discriminated from each other. The water absorptive polymer and the thickener are preferably such that they repeat absorption and release of water with variations in temperature thereby to enable temperature control.

While it is possible to use organic matter as exothermic material in the first method of the invention, metal powders which do not generate offensive odor as a reaction progresses are used including iron powder, zinc powder, aluminum powder, and magnesium powder, or powder of an alloy comprised of two or more kinds of such metals, or a mixture powder of such metal powders. Of these metal powders, iron powder in particular is preferably used when all such factors as safety, ease of handling, cost, keeping quality, and stability are considered. For the carbon component, carbon black, graphite, and activated carbon may be exemplified as such. and for the metal chloride, alkali metal chlorides, such as sodium chloride and potassium chloride, and alkali earth metal chlorides, such as calcium chloride and magnesium chloride, may be exemplified as such.

The inorganic or organic water retainer is an agent for retaining water such that not only does it function to release water when the exothermic reaction slows down, it acts to increase voids in the exothermic composition thereby to enable a favorable contact between the ambient air and the exothermic composition.

Specific examples of such water retainer are perlite, cristobalite, vermiculite, siliceous porous substances, silicates, such as calcium silicate, siliceous earth substances, such as silica, diatom earth, and alumina, mica powder, clay, magnesium oxide, such as talc, etc., silica powder, wood powder, and pulp powder.

For the pH adjustor, surface active agent, and defoaming agent, a conventional pH adjustor, such as sodium polyphosphate, and other materials used in the art are used as such.

In the fluid exothermic composition, where an excess water is present, part of the water may be caused to be absorbed by the base material and/or the covering material.

It is desirable that the base material and/or the covering material should have a water absorbing characteristic. However, materials having a water absorbing characteristic are not particularly limited as long as the material is water-absorbable and has a thin sheet configuration. Specific examples of such material are foamed thin sheet, paper, card board, card board core material, nonwoven fabric of rayon or the like, woven cloth, or porous thin sheet.

In the first method of the invention, the base material and the covering material may be basically of the same type, but since the exothermic composition which generates heat through its contact with air is the heat source of the device, it is required that at least one or part of the base material and the covering material must be gas permeable.

In the formation of such an ultra-thin exothermic device, if any further thickness reduction (to a thickness of about 1 mm or less) and weight reduction are intended, there will occur a decrease in the quantity of exothermic reaction per unit hour. Therefore, only with a pressure reduction based on the consumption by the exothermic composition of oxygen in the air within the pouch, it may not necessarily be possible to maintain such a condition of reduced pressure as is sufficient to prevent any movement and/or displacement of the exothermic composition. In such a case, it is desirable that the whole or part of the exothermic composition be fixed to the base material and/or the covering material so that the exothermic composition can be prevented from movement and/or displacement Specifically, where the base material and/or the covering material has a smooth surface, for example, it is desirable that a concave-convex portion be physically formed on the surface at least at a site of contact with the exothermic composition, or a water absorber having a water absorbing capability be laid on one side or both sides of the base material and/or the covering material thereby to form a concave-convex portion at a site of contact of the base material and/or the covering material with the exothermic composition. Thus, the bond of the base material and/or the covering material with the exothermic composition can be increased to prevent the exothermic composition from movement and/or displacement because of the adhesion resulting from water absorption from the exothermic composition and the concave/convex portion formed as shown above.

The water absorber is not particularly limited as long as the water absorber, whether or not its material has a water absorption characteristic, is in effect water absorptive. Specific examples of the water absorber is one comprised of foamed sheet, paper, card board, card board core material, nonwoven fabric of rayon or the like formed of water absorptive fibers, woven cloth, or a porous thin sheet; one comprising a foamed thin sheet, paper, nonwoven cloth, woven cloth, or a porous thin sheet which is made to contain or carry a water absorbing agent by impregnation, loading, or transfer thereby so as for it to have a water absorbing characteristic; and one comprising a combination of a foamed film sheet, paper, nonwoven cloth, woven cloth, or porous thin sheet and a water absorptive foamed thin sheet, paper, nonwoven cloth, woven cloth, or a porous film/sheet cut to a planar configuration of the exothermic composition, the combination being placed on the exothermic composition to obtain a water absorbing characteristic.

In the first method of the invention, since the base material and/or the covering material is formed, at least at a site of contact with the exothermic composition or at water absorbers, with a water absorptive layer which is made to contain or carry a water absorbing agent by impregnation, loading, or transfer, it is desirable to embed the whole or part of the exothermic composition in the concave/convex portion and/or the water absorptive layer thereby to prevent any movement or displacement of the exothermic composition.

In the first method of the invention, in order that any movement or displacement of the exothermic composition may be more positively prevented, it is desirable that at sites of contact with the exothermic composition in both the base material and the covering material there should be formed concave/convex portions and/or water absorptive layers, so that part of water in the exothermic composition, that is, excess water may be absorbed through the concave/convex portions into the base material and/or the covering material.

Since the movement of the exothermic composition within the pouch is prevented in this way, the exothermic composition can be prevented from being displaced toward one side, with the result that variations in heating temperature and generation of an abnormally high heat are inhibited.

In the case where the surface of the base material and/or the covering material is smooth, the method to be employed for roughing (to form concavities and convexities on) the surface of the base material and/or covering material is not particularly limited. Specifically, however, it is desirable to roughen the surface (to form concavities and convexities thereon) by a physical treatment, for example, a corona treatment thereby to enable the surface to exhibit a wetting index of at least dyne or more, preferably 40 dyne or more.

In the first method of the invention, where at least the site for contact with the exothermic composition in the base material and/or the covering material is formed with a roughened surface or a concavity and a convexity and/or with a water absorptive layer, the base material and/or the covering material, if it is formed of a water absorptive material, the roughened surface or concavity/convexity functions to prevent the displacement or movement of the exothermic composition, and the water absorptive layer also functions to prevent the movement or displacement of the exothermic composition, whereby a synergistic effect can be obtained in more positively preventing the movement or displacement of the exothermic composition. Furthermore, part of the water in the exothermic composition, that is, excess water is allowed to be absorbed by the base material and/or the covering material.

Where a water absorptive layer is formed in the base material and/or the covering material at a site for contact with the exothermic composition, other ingredients than water of the exothermic composition are attracted by the water-absorbing force of the water absorptive layer toward the base material and/or the covering material, and part of such ingredients wets out on the water absorptive layer to produce a powerful anchor effect. In that case, therefore, any particular surface roughing treatment is unnecessary.

For the water absorptive agent, aforementioned water absorptive polymers and thickeners are exemplified as such. Therefore, the water absorptive layer is a layer formed of any of those polymers or thickeners.

As already stated, the base material and/or covering material used in the first method of the invention embraces such a material of a single layer construction and one comprised of plural layers laminated one over another in the direction of thickness of the layer.

In the above connection, the expression "laminated" means that individual layers are wholly or partially bonded together by lamination or otherwise, and also that individual layers are simply laid one over another and, at a local site, such as a peripheral edge portion or a central portion, they are joined together by heat setting, bonding, adhesion, hot fusion bonding, or lamination.

Where the base material and/or the covering material is of a single layer construction (single film or sheet), as earlier described, in order to prevent movement and/or displacement thereof, it is desirable that the surface of the thin sheet, if flat and smooth, be roughened (concave-convex surfaced), or a foamed thin sheet, paper, nonwoven fabric, woven fabric or porous thin sheet be used as the thin sheet. Where these are water-absorbable materials such that the material is comprised of water-absorbable fibers, for example, such material may be caused to contain or incorporate by way of impregnation, transfer, lamination, or loading thereby to exhibit a water absorption behavior. In this case, use of a foamed thin sheet such as sponge, nonwoven fabric or woven fabric will provide good adhesion with an adhesive layer to be described hereinafter. Where the base material comprises plural layers, that is, two or more layers of the thin sheet laminated together, the earlier noted ones may be mentioned as typical examples.

Both the base material and the covering material must have necessary mechanical strength characteristics such as tensile strength, and preferably they are flexible as a whole to provide improved conformability in relation to foot surface.

Therefore, the base material and the covering material may vary considerably in thickness depending upon the intended use and are not particularly limited in thickness. Specifically, the thickness is generally in the range of from 5 to 5000 $\mu$m or so, and where the device is applied directly to the user's foot, a preferred thickness range is from 10 to 1500 $\mu$m, more preferably from 20 to 1000 $\mu$m. For general use, a thickness range of from 5 to 2500 $\mu$m is preferred, more preferably from 10 to 2000 $\mu$m.

A thickness of less than 5 $\mu$m with respect to the base material and the covering material is undesirable because it does not provide necessary mechanical strength and may make it difficult to equalize the layer thickness. Where the thickness of the base material and of the covering material exceeds 5000 $\mu$m, these materials are of low flexibility even if they are comprised of a foamed material such as sponge, and their conformability in relation to the surface of the user's foot is exceptionally low. Further, they feel rough and present unfavorable hand. A further inconvenience of such a layer thickness is that the foot warming exothermic device as a whole becomes excessively thick.

Therefore, it is particularly preferable that both the base material and the covering material are within a thickness range of from 15 to 1000 pm, because this thickness range provides necessary mechanical strength and good flexibility.

The base material and the covering material may be a foamed or non-foamed thin sheet formed from a polymeric material. Where a foamed thin sheet is used, the exothermic composition can be caused to bite into the thin sheet, being thereby prevented from movement and displacement.

Examples of the component polymeric material of such thin sheet are polyethylene, polypropylene, polyamide, polyester, polyvinyl. chloride, polyvinylidene chloride, polyurethane, polystyrene, saponified ethylene-vinyl acetate copolymer, and ethylene-vinyl acetate copolymer.

For enabling the non-foamed thin sheet formed of a polymeric material to have gas permeability, a number of methods can be used including a method such that vents are formed through a drawing operation during the process of forming the sheet, another method such that vents are formed by extracting a particular ingredient from the thin sheet, and a further method such that after the thin sheet is formed as such, vents are mechanically formed by a piercing operation such as punching and needling. A porous thin sheet can be obtained by any of these methods.

There are different types of foamed thin sheets comprised of a polymeric material, including foamed thin sheets of the type having closed cells or open cells formed by foaming which are open on opposite surfaces; those of the type in which after the process of foaming, the thin sheet is pressed whereby closed cells or open cells formed therein are fractured to be enabled to communicate with the opposite surfaces, the thin sheet being thus made gas permeable; and those of the type having no gas permeability and remaining gas-tight even after being foamed.

Paper and cloths such as woven cloths, knitted cloths, and nonwoven cloths are gas permeable because they are of such a construction that they have vent pores and/or vent paths formed therein which communicate with opposite surfaces. Fibers usable as component fibers of such cloths include, for example, natural fibers, regenerated fibers using natural fiber materials such as viscose fibers, semi-synthetic fibers, synthetic fibers, and mixtures of two or more kinds of these fibers.

The natural fibers include vegetable fibers such as cotton and hemp, and animal fibers such as silk and animal hair. Polymeric materials as components of the synthetic fibers include, for example, polyethylene, polypropylene, polyamide, polyester, polyvinyl chloride, polyvinylidene chloride, polyurethane, polystyrene, saponified ethylene-vinyl acetate copolymer, and ethylene-vinyl acetate copolymer.

In the first method of the invention, in order to enable the foot warming exothermic device to be more suitably applied to the user's foot at a curved portion, an extensible portion, and/or a flexing portion thereof, and to more readily conform to the movement of the extensible portion and also of the flexing portion, it is desirable that the base material and covering material, that is, the wrapper of the device, is formed of an extensible material, more particularly a stretchable material.

In other words, where the base material and covering material, that is, the wrapper is formed from an extensible material, more particularly a stretchable material, the wrapper exhibits good stretch/shrink characteristics such that it can more easily conform to the movement of various portions of the user's foot, such as curved portion, stretchable portion, and flexing portion, while keeping good contact therewith. Further, the wrapper does not feel stiff, nor does it give any unharmonious feel, thus enabling the device to give a comfortable feel when it is used. Moreover, separation during the use of the device can be positively prevented, which results in improved heating effect.

Examples of such extensible materials suitable for use as the base material and covering material are materials formed of synthetic resins having high extensibility, such as polyethylene and polypropylene.

Stretchable materials for the base material and covering material, that is, stretchable thin sheets, are not particularly limited as long as the thin sheets are formed from materials having stretch/shrink characteristics. Specifically, however, typical examples of such materials are foamed thin sheets, nonwoven cloths, woven cloths, or porous thin sheets which have stretch and shrink characteristics and high adaptation for bond with the exothermic composition. These materials are preferred as long as they have a water absorptive ability, or if they are provided with a water absorptive ability or improved water absorptive ability by having been caused to contain, incorporate or carry by impregnation, deposition, loading, or transfer, whether or not they have a water absorptive ability. The reason is that such material is operative to absorb an excess water in the exothermic composition to eliminate any barrier layers thereby to keep the exothermic composition in a favorable condition.

Materials suitable for stretchable thin sheets include, for example, natural rubber, synthetic rubber, and thermoplastic elastomers. Thermoplastic elastomers are preferred inter alia because they have high stretch/shrink characteristics, are easy to handle, and have hot fusion bonding properties, which can facilitate the manufacture of the exothermic device.

In the first method of the invention, of course, irrespective of whether or not the base material and covering material have adhesivity, and hot fusion or hot welding properties, it is desirable that the base material and the covering material be sealingly secured around the exothermic composition by adhesion, hot fusion bonding, or heat bonding. Specific examples of the synthetic rubber are butadiene rubber, isoprene rubber, styrene-butadiene rubber, acrylonitrile-butadiene rubber, chloroprene rubber, isobutylene-isoprene rubber, polyalkylene sulfide, silicone rubber, poly (chlorofluoroethylene)1 vinylidene fluoride-6 propylene fluoride copolymer, urethane rubber, propylene oxide rubber, epichlorohydrin rubber acrylate-acrylonitrile copolymer, and acrylate-2-chloroethyl vinyl ether copolymer.

Specific examples of the thermoplastic elastomer are olefinic elastomers, polyurethane elastomers, and polyester elastomers.

Specific examples of the olefinic elastomers are ethylene-propylene copolymer, ethylene-propylene-diene terpolymer, chlorosulfonated polyethylene, chlorinated polyethylene, and ethylene-vinyl acetate copolymer.

In addition to the case where a foot warming exothermic device is applied in direct contact with the user's foot, sometimes there may be cases where such a device is used through application to the exterior of a sock or application to the sole of a shoe. Therefore, unlike other types of exothermic devices which are applied to other sites, such as the waist, of a human body, the foot warming exothermic device is subject to considerable variations in the condition of air supply to the device depending upon the condition in which the device is applied and the condition of use, e.g., use during walking or while the shoe remains off.

That is, the foot warming exothermic device is subject to variations in the force of pressure which is applied thereto by walking and otherwise so that, where the wrapper is formed from a foamed material such as sponge, the space within the wrapper itself is increased or decreased accordingly. As a result, a kind of pumping action occurs such that the quantity of air feed to the exothermic composition tends to become greater than that in the case of exothermic devices for application to other sites of a human body, Therefore, the moisture permeability of the wrapper may be limited to a lower level than that of a wrapper for other types of exothermic devices for application to other sites than the foot. Thus, the wrapper may be comprised of a single-sided thin sheet having gas permeability, or may be so constructed as to have gas permeability with respect to only part of the both sides or one side thereof.

Then, if it is feared that the interior temperature of the exothermic device itself might rise too high to cause a low temperature burn, it is desirable that the water absorptive polymer and/or thickener should release moisture retained therein to form barrier layers or the like to suppress an exothermic reaction thereby to lower the temperature. Conversely, if the interior temperature of the exothermic device itself drops to the extent that the desired warming effect cannot be obtained, it is desirable that the water absorptive polymer and/or thickener be allowed to absorb free moisture to eliminate the barrier layers thereby to provide good contact with air.

In the first method of the invention, it is required that at least one or part of the base material and covering material must be gas permeable. Gas permeability has great bearing upon the control of reaction rate of the exothermic composition and/or of exothermic temperature and, therefore, control of gas permeability is desired in order to obtain effective warming effect and to prevent any low temperature burn to secure safety. For high precision control of gas permeability it is desirable to control film gas-permeability on the basis of moisture permeability. Specifically, the moisture permeability should be within a range of from 50 to 10,000 $g/m^2 \cdot 24$ hr, more particularly from 100 to 5,000 $g/m^2 \cdot 24$ hr, in accordance with the ASTM method (E-96-80D Method).

A moisture permeability of less than $50 g/m^2 \cdot 24$ hr is undesirable because the quantity of heat generation obtainable is too small to provide sufficient warming effect. A moisture permeability of more than 10,000 $g/m^2 \cdot 24$ hr is also undesirable, because it will cause an excessive rise in exothermic temperature which may lead to a low temperature burn. Therefore, the moisture permeability range of from 100 to 5,000 $g/m^2 \cdot 24$ hr with respect to the gas permeable thin sheet is particularly preferred, because this moisture permeability range enables heat generation of fine optimum temperatures which provide sufficient warming effect and at which there is no danger of low temperature burn.

Method of constructing the base material or covering material in such a way that part of the material has gas permeability is not limited to any particular method. For this purpose, however, in the case where the base material or covering material which is gas permeable is of a single layer, for example, the base material or covering material may be partially sealed with adhesive over the surface thereof, or in the case where the gas-permeable base material or covering material is of the laminated type, separately provided partial pieces of a thin sheet may be laminated over the material to partially cover such pores.

In the first method of the invention, the use of a fluid exothermic composition enables lamination of a layer by transfer, printing, spraying, coating or the like to a thin sheet thickness of the order of, for example, from 0.02 to 1.5 mm, preferably from 0.1 to 1.00 mm, further enabling lamination of individual layers to a uniform thickness. This provides for the realization of high speed processing, high precision control of the deposited areas, thin sheet oriented production, and equalization of film is thickness.

In this case, the fluid exothermic composition performs a function similar to that of adhesive in joining the base material and the covering material together and, therefore, the materials need not necessarily be sealingly bonded around the exothermic composition. However, in order to further improve the quality and reliability of the foot warming exothermic device, it is desirable that the base material and the covering material be sealingly bonded by heat bonding, adhesion, or hot fusion bonding around the fluid exothermic composition.

In the first method of the invention, the predetermined area in which the fluid exothermic composition is placed by lamination may be configured to cover a desired site of a foot. Examples of such a site include part of the sole of a foot; the whole of the sole; part of the instep of the foot; the whole of the instep; part or the whole of the sole or instep and part or the whole of a side portion of the foot; and part or the whole of the sole of the foot, part or the ~whole of a side portion, and part or whole of the instep.

Examples of part of the sole of the foot include toes, base of the toes, ball of the foot, plantar arch, and heel. Examples of the configuration of a foot warming exothermic device covering the sole of the foot are semicircle and semi-ellipse. Examples of the configuration of base material and covering material for covering the base of the toes, ball of the foot, plantar arch and heel are rectangle, square, trapezoid, oval, ellipse, circle, semi-ellipse, and horseshoe.

For covering the entire sole of the foot, the device may be configured like an inner sole cover of a shoe. Another example of covering configuration may be that a bulge corresponding to the plantar arch portion of the inner sole cover protrudes from a compressed portion of the inner sole cover which corresponds to the plantar arch of the foot.

In this case, for example, it may be understood that the plantar arch has a certain height when viewed from side. Therefore, the configuration of an exothermic device which covers the entire sole of the foot may be considered to be a configuration that covers the sole of the foot to be described hereinbelow, more particularly the whole plantar portion of the foot sole and part of sides of the foot. An example of the configuration of an exothermic device which covers part or the whole of the sole and part of side portion of the foot may be a configuration such that the device covers the whole of the sole and a portion extending from the sole around the heel and up to the ankles, more particularly a portion extending rearward of the ankles. In this case, the device may be so formed as to have such a configuration that the portion corresponding to the sole is shaped like an inner sole cover and that the portion covering that portion of the foot which extends around the heel toward the ankles, that is, the portion extending rearward of the ankles, comprises a bulge formed in continuation to the portion of the inner sole cover shape. The base material and covering material are readily deformed to conform to the bulged contour of the heel in response to the bulge of the heel.

Where the base material and covering material have extensibility and/or stretch-shrink characteristics, the base material and covering material are readily deformed to well conform to the bulge of the heel, for example, by becoming partially extended in corresponding relation to the bulge. In this way, the base material and covering material are well deformable so as to conform to complex concave/convex configuration of the foot, exhibiting improved conformance to configurational changes.

To cover part or the whole of the sole and part or the whole of side portions of the foot, the device may have a configuration such that it covers the whole of the sole or the back of the toe portion and a portion of the foot which extends therefrom and around the toe portion and up to the instep side portion of the toes. In addition, the device may take a tabi-like configuration or a sock-like configuration.

The configuration of the device in which the device covers the whole of the sole or the back of the toe portion and a portion extending therefrom and around the toe portion and up to the instep side portion of the toes is, for example, such that the device has a bulge portion formed in continuation to the inner sole cover-like portion which covers the whole of the sole, the bulge portion covering the toe portion and the instep side portion of the toes. In this case, the bulge portion extends in conformity to depressions and projections of the toes and irrespective of difference in size of such depressions and projections whereby the bulge portion is deformed to intimately follow the complex irregularities of the toes.

The "tabi" configuration or sock configuration may be one such that a sock divided symmetrically into two parts continued with each other along a center line of the bottom is folded centrally of the bottom after lamination is effected and portions extending from the toe through the instep to the ankles are joined at edges thereof with edges of portions extending from the heel to the ankles. Another configuration example may be such that a portion of the sock extending from the ankles toward the toe is divided into two parts which are connected centrally of the bottom to each other, and a bulge is formed in continuation centrally with a rear end portion of the bottom for covering the heel up to the ankles. After lamination is effected, side edges of the bulge are joined with rear edges of the portions extending from the ankles to the toe portion, and the side edges of the portion extending from the ankles to the toe portion are joined together.

Of course, the base material and covering material are not particularly limited in configuration and size as long as they are larger in configuration and size than the exothermic composition laminated on the base material. Specifically, however, it is desirable that the base material and covering material are similar or substantially similar in configuration to the fluid exothermic composition placed in position and are formed larger than the exothermic composition in such a way that they have an extension of the order of few mm to 20 mm extending beyond the circumference of the exothermic composition in all directions.

Where masses of the fluid exothermic composition are laminated on the base material at plural sites, the base material and the covering material may be bonded together by means of the fluid exothermic composition. Of course, in order to assure improved quality and improved reliability with respect to the foot warming exothermic device, it is desirable that the base material and the covering material are sealingly joined by heat bonding, adhesion, or hot fusion bonding around the fluid exothermic composition.

The method of forming the base material and covering material to the predetermined configuration is not particularly limited, but such forming may be performed when the base material, covering material, and fluid exothermic composition are laminated together, or may be carried out thereafter by, for example, punching or fusing.

In any such method, from the standpoint of reducing the number of operating stages and the time of operation thereby to achieve cost reduction, it is presumed that circumferential edges of the base material and covering material are joined together by heat setting or heat sealing, and therefore it is desirable that punching or fusing be carried out by heat setting rollers or heat sealing rollers concurrently with the process of bonding.

With the foot warming exothermic device of the invention in which a bulge is provided in continuation to the device, the exothermic composition is placed in a thin sheet fashion between the base material and the covering material, both of which have flexing characteristics, and therefore the device is formed thin as a whole. This enables the bulge to be readily deformed in corresponding relation to the recess of the plantar arch, so that the bulge can well conform to the recess of the plantar arch to efficiently warm the entire sole of the foot.

As described above, in the first method of the invention, the fluid exothermic composition is laminated by printing or coating on the surface of the base material, and this permits the fluid exothermic composition to be laminated in a thin sheet fashion and uniformly. However, the fluid exothermic composition may also be formed partially thick to provide a finger-pressure treatment-like effect in addition to the heating effect.

That is, it is possible to laminate at least one time on part of the surface of the fluid exothermic composition another layer of the fluid exothermic composition to form a partially thick portion, or to place at least a metal powder selected from among the metal powder, a water absorber, and a carbon component, by transfer or spraying on part of the surface of the fluid exothermic composition laminated on the base material thereby to render the exothermic composition thick in part.

In this way, by making the fluid exothermic composition thick in part it is possible to control the distribution of heat generation, or by making the fluid exothermic composition thick at a site such as at the tip of the toe which is sensitive to cold, it is possible to enhance the effect of warming. Further, it is possible to arrange that at least a metal powder selected from among the metal powder, a water absorber, and a carbon component is transferred or sprayed on the exothermic composition to form barrier layers, thereby to cause the metal powder to absorb moisture forming the barrier layers so that an initial temperature rise of the foot warming device can be accelerated when the device is taken out from a gas-tight outer pouch.

In this case, the fluid exothermic composition placed on the surface of the base material may be locally formed thick at a position corresponding to the recess of the foot and/or the vicinity thereof to provide a favorable thermotherapy-like and/or toe pressure treatment-like effect.

of course, the number of sites at which the fluid exothermic composition is formed thick is not limited to one, and the composition may be placed thick at two or more sites.

Further, in the first method of the invention, it is desirable that at any suitable time point prior to a finished foot warming exothermic device is enclosed into an air-tight outer pouch, an adhesive layer has been formed on an exposed surface of one of the base material and the covering material, the other material being partially gas permeable, because such arrangement permits the foot warming exothermic device to be adhesively attached securely to the foot surface or a sock or a shoe.

The adhesive layer is not particularly limited as long as it is adhesively attachable to foot surface, sock, and shoe. Specifically, for example, a wet pack medication layer or a layer formed of adhesives to be described hereinafter may be mentioned as such.

Adhesives usable in forming such an adhesive layer include, for example, solvent-type adhesives, emulsion type adhesives, and hot-melt type adhesives. Specific examples of these adhesives are rubber-based adhesives, vinyl acetate-based adhesives, ethylene-vinyl acetate adhesives, polyvinylalcohol-based adhesives, polyvinylacetal-based adhesives, vinyl chloride-based adhesives, acrylic adhesives, polyamide-based adhesives, polyethylenic adhesives, cellulose-based adhesives, polysulfide adhesives, and hot-melt type polymeric containing adhesives.

Specific examples of hot-melt type adhesives include A-B-A type block copolymer, saturated polyester high polymer, polyamide high polymer, acrylic high polymer, urethane high polymer, polyolefin high polymer, and polyolefin copolymer, modifications these materials, and a mixture of two or more kinds of these materials.

The modifications are those hot-melt high polymers part of which is replaced by other component in order to improve their properties such as tackiness or stability.

In A-B-A type block copolymer, A block is a monovinyl replaced aromatic compound A such as styrene or methyl styrene which is an inelastic polymer block, and B block is an elastic polymer block of conjugate diene such as butadiene or isoprene. Specific examples include styrene-butadiene-styrene block copolymer, and styrene-isoprene-styrene block copolymer, and a mixture thereof.

Commercially available ABA type block copolymers include Califlex TR-1101, Califlex TR-1107, Califlex TR 1111 (manufactured by Shell Chemicals, and Solprene 418 manufactured by Phillip Petroleum.

Of the foregoing adhesives, rubber-based adhesives, acrylic adhesives, and adhesives containing hot-melt type high polymer material are preferred, since an adhesive layer comprised of such adhesive can adhere well to a surface such as, foot surface, sock or shoe. More particularly, an adhesive layer containing a hot-melt type high polymer material is preferred because it exhibits good initial tack, and also exhibits very high adhesion during heat application.

The thickness of the adhesive layer is not particularly limited, but a thickness range of from 5 to 1000 $\mu$m is preferred, especially from 10 to 500 $\mu$m, more preferably from 15 to 250 $\mu$m. If the thickness of the adhesive layer is less than 5 $\mu$m, it is difficult to obtain the required adhesion strength. A layer thickness of more than 1000 $\mu$m is not only meaningless but uneconomical.

In the first method of the invention, where an adhesive layer is formed on an exposed surface of the foot warming exothermic device, it is desirable that the exposed surface of the base material or covering material be roughened or be comprised of paper, card board, card board core material, woven fabric, nonwoven fabric of rayon or the like, or rough-surfaced thin sheet such as foamed thin sheet in order to provide increased strength of bond of the adhesive layer with the base material or the covering material.

In the first method of the invention, where an adhesive layer is formed on one surface of the exothermic device as above said, the adhesive layer contains or carries at least one of compress medication, far infrared radiator, magnetic material, and skin absorbable medication as desired. Thus, in addition to the warming effect of heat generation of the exothermic device for improvement of general physical functions including blood circulation, various other effects can be obtained including compress medication effect, far infrared radiation effect, magnetic treatment effect, and endermic effect, and all these effects can operate synergistically to enhance general or local therapeutic effect.

The skin absorbable medication is not limited as long as it is skin absorbable. Specific examples thereof include a skin stimulant, anodyne/antiphlogistic, central nerve active agents (soporific/sedative, psychoneurotic agent, etc.), diuretic, hypotensive, coronary vasodilator, antitussive/expectorant, antihistaminic, anti-arrhythmic, cardiac, adrenocortical hormone drug, local anesthetic, and an organic acid such as acetic acid which is a medicament for athlete's foot. Of course, one type of these medicines, or a blend of two or more types thereof, may be used as required.

The amount of skin absorbable medication used is not limited as long as a medical effect is expected but, from the point of view of pharmacological effect and economy, and from the point of view of adhesion, the amount of medication may be suitably determined within the range of from 0.01 to 25% by weight, more particularly from 0.5 to 15% by weight, relative to 100% by weight of the adhesive.

The configuration of the far infrared radiator is not limited to a particular configuration. Specifically, for example, the radiator may be a formed mass which can serve as a toe press agent to provide a toe pressure effect. However, in order to enhance the flexibility of the foot warming exothermic device and its ability to conform to the foot surface, it is preferable that the far infrared radiator be of powder form.

As described above, the first method of the invention uses an exothermic composition viscosified in a fluid form which has exceptionally high fluidity in contrast to the prior art exothermic composition which has a wetting characteristic and is of powder form. This permits the exothermic composition to be laminated by printing or coating on base material as supplied at high velocity, the lamination being performed in succession and accurately, uniformly and very thin within a predetermined space.

Therefore, the fluid exothermic composition can be laminated very thin on the base material. This makes it possible to provide an ultra-thin foot warming exothermic device such that its thickness poses no problem when the device is placed in a shoe. Since the foot warming exothermic device can be made to such an extra thin size, the invention provides exceptionally good advantages that the device has good flexibility and presents no unharmonious feel when in use, and that the device can well conform to any complex concave and convex configuration, such as curves and bends, at the desired site of the foot.

The fluid exothermic composition can be accurately laminated within the predetermined space on the base material, and this enables the fluid exothermic composition to be accurately distributed in a space corresponding to the desired site of the foot without waste. Since warming heat can be efficiently applied in this way to the desired site of the foot which requires warming, good warming effect can be obtained and general physical functions including blood circulation can be effectively enhanced. In addition, the fluid exothermic composition does not involve any such dissipation of powder of the exothermic composition as has hitherto been experienced, and enables such plant management as will meet the GMP standards in the manufacture of medical tools and medicament in the future.

Further, as already stated, the fluid exothermic composition can be uniformly laminated on the base material, and this prevents the development of any abnormal high temperature point or abnormal high temperature site due to unbalanced distribution of the exothermic composition and generation of a low temperature burn as well, thereby enhancing safety in use.

The first method of the invention uses a fluid exothermic composition which can easily be transferred by printing, coating or the like and enables the manufacture of an ultra-thin foot warming-exothermic device at high rate. Moreover, in contrast to the case with prior art exothermic compositions, where the exothermic composition contains any excess of water, the excess water forms water barriers to diminish air supply and substantially stop the exothermic reaction, with the result that various harmful problems due to such occurrences as heat generation loss in the process of manufacture, and quality degradation and coagulation of the exothermic composition can be effectively prevented.

In the first method of the invention, the fluid exothermic composition is laminated by printing or coating on the surface of the base material in at least one predetermined region and in such a configurational pattern as to cover the desired site of the foot, and thereafter the thin sheet covering material is placed thereon so as to cover the exothermic composition. In this case, for example, by guiding the covering material by rollers onto the base material and the fluid exothermic composition supplied at high rate, the covering material can be placed on the base material and the fluid exothermic composition without stopping the run of those materials. In the first method of the invention, as is the case with the prior art, after the covering material is placed in position, the exothermic device is formed to the predetermined configuration, and the so formed exothermic device is enclosed in a gas-tight pouch, but the formation of the exothermic device and enclosure of the same into the gas-tight pouch can be Carried out in unison with the placement of the covering material.

Therefore, according to the first method of the invention, it is possible to manufacture and package the foot warming exothermic device by actuating, in unison with the feeding of the base material, a fluid exothermic composition laminating unit for laminating the exothermic composition, an exothermic device forming unit for forming the foot warming exothermic device, and a packaging unit for enclosing the foot warming exothermic device into a gas-tight pouch, for example, while feeding the base material continuously at a high speed on the order of 160 m or more per minute, several times faster than the prior art. This enables manufacture of the foot warming exothermic device on a volume production basis and at low cost.

Further, operating stages, including placing the fluid exothermic composition and covering material on the base material to form the foot warming exothermic device, forming the foot warming exothermic device into shape, and packaging the same, can be carried out on an integrated basis, for example, within a short period of time on the order of 0.1 to less than 1 second. Therefore, the manufacturing process involves no possibility of is creating any conditions which may permit heat generation of the exothermic composition, and thus heat generation of the exothermic composition in the manufacturing process can be completely prevented.

Accordingly, it is possible to completely eliminate possibilities of such occurrences as exothermic loss, quality degradation and coagulation of the exothermic composition which may otherwise be caused due to heat generation in the manufacturing process. Thus, various harmful effects such as decreased yield, handling difficulty, maintenance trouble with respect to the manufacturing equipment, limitations imposed on operating hours of the manufacturing equipment and/or on working hours of operators, and difficulty involved in the treatment of coagulated matter. Hence, high quality and highly dependable exothermic devices can be produced at lower cost.

Moreover, in such high speed manufacturing operation, the base material feed unit, paste-like exothermic composition laminating unit, covering material laminating unit, forming units, such as punching unit for foot warming exothermic device. and packaging unit for enclosing the foot warming exothermic device into a gas-tight pouch can be continuously operated for manufacturing operation. Therefore, in contrast to the prior method of manufacturing a foot warming exothermic device in which all such machines must be intermittently operated in placing a fluid exothermic composition on a base material, it is only required that adjustment be made to synchronize these units in their operating velocity. Any timing adjustment is no longer necessary with respect to operations of the different units. Only very simple control adjustment is required. Thus, means for controlling operation timing with respect to individual units, and the construction of each unit is simplified.

In the first method of the invention, where the base material and covering material have extensibility and/or stretch and shrink characteristics, the exothermic device can more easily conform to complex concave and convex configuration of the foot at the desired site. The adaptability of the device to variations of the concave and convex configuration due to movement of the foot can be enhanced. Separation or floating of the foot-warming exothermic device from the site of application is positively prevented. Thus, any decrease due to such separation or floating in the warming effect of the device and in the promoting effect of general physical function including blood circulation can be prevented.

In the first method of the invention, where the base material and/or covering material is water absorbable, the excess water in the fluid exothermic composition is caused to be absorbed by the base material and/or covering material prior to use whereby the proportion of water in the exothermic composition can be adjusted to a proportion suitable for heat generation. Therefore, by breaking the gas-tight pouch before use it is possible to cause heat generation to start at once whereby necessary exothermic temperature can be promptly obtained. Further, water evaporated from the exothermic composition as exothermic reaction progresses can be replenished by moisture release from the base material or the covering material, whereby the required exothermic temperature can be retained for a long period of time.

In the first method of the invention, where the base material and/or covering material are/is water absorbable, as the material absorbs excess water in the fluid exothermic composition, the exothermic composition is drawn toward the base material and/or covering material, so that part of the fluid exothermic composition bites into the base material and/or covering material to produce an anchoring effect through which the fluid exothermic composition can be fixed to the base material and/or covering material.

Therefore, in contrast to the prior art method in which the exothermic composition is fixed within the wrapper by utilizing the reduced pressure due to an exothermic reaction, the fluid exothermic composition can be positively immobilized. This, coupled with the fact that the foot warming exothermic device is formed ultra-thin, positively prevents movement or displacement of the fluid exothermic composition within the wrap. As a result, for example, it is no longer necessary to shake the foot warming exothermic device by hand when using it to eliminate uneven distribution of the exothermic composition. Thus, the method of use is simplified, and the development of any abnormal high temperature spot or portion resulting from maldistribution of the fluid exothermic composition can be surely prevented. Thus, occurrence of a low temperature burn can be prevented and safety in use can be more enhanced.

In the first method of the invention, for example, where the fluid exothermic composition is formed partially thick because of a separate layer of fluid exothermic composition laminated is thereon, or where at least metal powder, selected from metal powder, water absorber, and carbon component, is laminated on part of the surface of the fluid exothermic composition, so that the exothermic composition is made partially thick, it is possible to increase the quantity of heat generation at the thicker portion, develop a therapeutic toe pressure, and/or prompt a rise of initial temperature.

In such a case, therefore, the thickness of the layer is locally thick, particularly at a particular recess portion of the foot and in the vicinity thereof, to provide a thermotherapeutic effect, and enhance warming effect at a site sensitive to cold, such as the toe portion. Furthermore, through control of exothermic temperatures, it is possible to prevent occurrence of a low temperature burn, and enhance safety in use.

In the first method of the invention, where an adhesive layer is formed on the exposed surface of one of the base material and the covering material and at least part of the other is gas-permeable, the adhesive layer may be applied directly to the skin of the foot, or to the sock or the sole of a shoe. Thus, the foot warming exothermic device can be readily fixed to the foot at the desired site.

In this case, where at least one of a far infrared radiator, magnetic material, and skin absorbable medication is contained in or carried by the adhesive layer, heating effect of the far infrared radiator, therapeutic effect of the far infrared radiator, therapeutic effect of the magnetic material, and therapeutic effect of the medication can be obtained. These effects, coupled with general physical function promotion effect, such as blood circulation enhancement, synergistically operate to provide even better results.

In order to achieve the aforementioned object, a second method of manufacturing a foot warming exothermic device of the invention (hereinafter referred to as second method of the invention) comprises: placing a fluid exothermic composition on a thin sheet base material, then placing on top thereof a thin sheet covering material, bonding said base material and said covering material together utilizing the viscous characteristic of said fluid exothermic composition, then punching the resulting laminate to such a shape as to cover a desired foot site, one of said base material and said covering material, or part of either one being gas permeable.

The second method of the invention will now be described. In the second method of the invention, a fluid exothermic composition is first placed on a thin sheet base material, and then a thin sheet covering material is placed thereon, the base material and the covering material being bonded together by virtue of the viscosity of the fluid exothermic composition, whereby a laminate is obtained.

Fluid exothermic compositions usable in this second method of the invention are similar to those in the first method of the invention. Therefore, detailed description of those compositions is not repeated here for the sake of brevity.

In the second method of the invention, as is the case with the first method of the invention, until excess moisture present in the fluid exothermic composition is absorbed by a water absorptive thin sheet, any oxidation reaction, that is, exothermic reaction, of the exothermic composition is inhibited, even when the exothermic composition comes in contact with air. Therefore, various harmful effects of any thermal loss due to a heat reaction in the stage of manufacture, and quality degradation and coagulation of the exothermic composition can be positively prevented. The fluid exothermic composition can be laminated to a uniform thickness. This, coupled with the bond of the exothermic composition with the wrapper, prevents movement and displacement of the exothermic composition. Any excessive thermal reaction of the exothermic composition can be also avoided.

In the second method of the invention, the method of laminating the fluid exothermic composition on the base material is not particularly limited. Specifically, however, coating by a coater such as head coater, roller, applicator or the like is exemplified as such. In the second method of the invention, it is essential that at least one of the base material and the covering material must be wholly or partly water absorptive. In other respects, the base material and covering material are not particularly limited as long as they are of thin sheet form. Specifically, for example, materials enumerated in the description of the first method of the invention may be mentioned as such. For the sake of brevity, however, detailed description thereof is omitted.

In the second method of the invention, the laminate obtained in the manner as described above is punched to a shape covering a desired site of the foot to give a foot warming exothermic device in which at least one or part of the base material and covering material is gas permeable.

In the second method of the invention, the laminate obtained in manner as described above is punched to a shape covering a desired site of the foot to give a foot warming exothermic device in which at least one or part of the base material and covering material is gas permeable.

The stage of punching the laminate to a predetermined shape may be carried out with the laminate kept at a rest. In that case, plural laminates arranged in the direction of laminate feed and in a transverse direction rectangular to the direction of laminate feed are punched simultaneously whereby a large number of foot warming exothermic devices can be formed at one time. The use of this method can result in a cost reduction.

This method, as already stated, is such that, for example, a fluid exothermic composition is laminated on a thin sheet base material being fed, and then a thin sheet form covering material is guided by rolls onto the laminate. Where the covering material is placed over the fluid exothermic composition to obtain a laminated exothermic sheet, punching operation is carried out at the stage of punching.

In this case, laminates a re arranged in a transverse direction rectangular to the direction of laminate feed, or arranged in staggered relation to both the direction of feed and the transverse direction are simultaneously punched on a continuous basis, whereby a larger number of foot warming exothermic devices can be completed, which means a larger cost reduction.

The laminate is punched out to such a configuration as to cover a desired site of the foot.

In the second method of the invention, each laminate obtained is punched to such a configuration as to cover a desired site of the foot. The configuration of the punched-out foot warming exothermic device is not particularly limited, but may be determined as desired. Specific examples of such configuration are same as those noted with respect the first method. For the sake of brevity, detailed explanation of such configurations is omitted.

In the second method of the invention, the base material and the covering material are adhesively joined together by virtue of the viscosity of the fluid exothermic composition, and thereafter excess water is absorbed into the base material and covering material. The resulting foot warming exothermic device is enclosed in a non-gas-permeable outer wrapper, in which state the device may be delivered as a commercial article to the distribution system.

However, it is desirable that the punched-out foot warming exothermic device be interposed between two thin sheets and, simultaneously with or after this interposition, the two thin sheets are punched out to a larger size than the foot warming exothermic device, and that before or simultaneously with or after this punching operation the two thin sheets are sealingly joined along the peripheral edge of the foot warming exothermic device.

In this case, at least one or part of the two thin sheets is gas permeable. In this way, a more reliable foot warming exothermic device is obtained.

Through the above described process is obtained a foot warming exothermic device of a desired configuration. The quantity of air supplied to the exothermic composition in the device is controlled through the gas permeability of the two thin sheets. Therefore, the control of gas permeability with respect to the exothermic composition is made on the basis of moisture permeability in the same manner as in the case of gas permeability control with respect to the base material and/or covering material in the first method of the invention. Referring to moisture permeability, it is noted that the moisture permeability of the laminated thin sheet including one of the two thin sheets and the base material or covering material is similar to the description given for the first method of the invention. For the sake of brevity, therefore, detailed description is omitted.

The two thin sheets may comprise a non-gas-permeable one and a gas-permeable one. They may have tackiness, heat adhesive characteristics, or hot fusibility.

A sheet having tackiness may comprise a base sheet and a gas permeable adhesive layer formed over the entire surface thereof, the adhesive layer being formed of a hot melt type adhesive, or may be one having a partially gas-permeable or gas impermeable adhesive layer formed all over the surface. Whether or not the base sheet itself has heat adhesivity or hot fusibility is not important.

In the second method of the invention, a foot warming exothermic device is interposed between the two thin sheets and, simultaneously with or after this interposition, the two sheets are punched out to a larger size than the foot warming exothermic device, and before or simultaneously with or after this punching operation the two sheets are sealingly joined along the peripheral edge of the foot warming exothermic device.

The punching operation may be made with a continuous foot warming exothermic device interposed between two sheets as held in a static condition. In this case, punching is made with plural continuous exothermic devices arranged in the direction of feed and those arranged in a transverse direction rectangular to the direction of feed, by punching them simultaneously. This permits a large number of exothermic devices to be punched at one time, which leads to cost reduction.

In the second method of the invention, after the continuous exothermic device has been made, two lengths of thin sheets are sealingly joined along the peripheral edge of the foot warming exothermic device prior to the punching of the continuous exothermic device or simultaneously with the punching of the continuous exothermic device, or after the punching of the continuous exothermic device.

In connection with the operation of punching into a larger size than the foot warming exothermic device, the larger size is not particularly limited as long as the size is larger than the size of the foot warming exothermic device. However, it is desirable that the punched out configuration is similar to the configuration of the foot warming exothermic device and is larger in size than the contour of the device, extending outward of the peripheral edge of the device on the order of a few mm to 20 mm.

In the second method of the invention, the extended portion is sealingly secured. That is, the two thin sheets are sealingly joined by adhesion, heat bonding or hot fusion around the peripheral edge of the foot warming exothermic device.

In the second method of the invention, an adhesive layer may be formed over the whole or part of the exposed surface of one of the laminate components and at least part of the other component is gas permeable.

In this case, where at least one compress medication, far infrared radiator, magnetic material, and skin absorbable medication is contained in or carried by the adhesive layer, effects similar to those in the first method of the invention can be obtained. Repetition of details about this is avoided for the sake of brevity.

In the second method of the invention, the fluid exothermic composition is laminated on the thin sheet base material, then the thin sheet covering material is placed on the laminate, whereby the base material and the covering material are joined together by means of viscosity of the fluid exothermic composition. Then, the resulting laminate is punched into such a shape as to cover a desired site of the foot. At least one or part of the base material or covering material is gas permeable.

Therefore, manufacture of an ultra-thin foot warming exothermic device is possible, and the use of the fluid exothermic composition enables formation of barrier layers by excess water which inhibits an exothermic reaction. Thus, the method prevents various problems which may otherwise arise from heat generation loss, quality degradation of the fluid exothermic composition, and coagulation of the composition in the stage of manufacture. Furthermore, the fluid exothermic composition is uniformly distributed within the pouch and immobilized therein, whereby movement and displacement of the fluid exothermic composition can be prevented. Thus, the possibility of excessive exothermic reaction of the exothermic composition is minimized so that the problem of low temperature burn is avoided and safety in use is enhanced.

The foot warming exothermic device of the invention is characterized in that it is manufactured according to the first method or the second method of the invention in order to achieve the foregoing objects. The configuration of the foot warming exothermic device is not limited. Specifically, however, the device may be so configured as to cover a desired site of the foot and, more particularly, to cover, for example, the sole of the foot, or part or the whole of the instep of the foot.

The foot warming exothermic device of the invention is manufactured by the first method or the second method of the invention, and is a high quality device of the kind and is highly reliable.

DETAILED DESCRIPTION OF THE PREFERRED EMBODIMENTS

Embodiments of the invention will now be described in detail with reference to the drawings. It is understood, however, that the invention is not limited to these embodiments.

Figure 1:
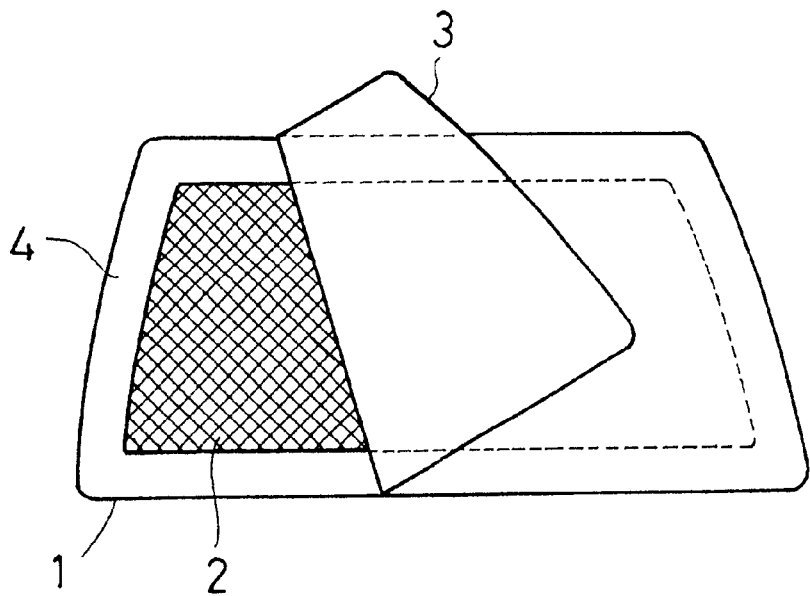
FIG. 1 is a plan view of a first embodiment of the present invention.

A first embodiment of the invention is one example of a method of manufacturing a foot warming exothermic device for warming the back of the toes of the foot according to the first method of the invention, and of a foot warming exothermic device manufactured by the method. FIG. 1 shows a plan view of the foot warming exothermic device.

This foot warming exothermic device was manufactured according to the following procedure. On a base material 1 having water absorbing power, as it was paid out, was screen printed as a fluid exothermic composition 2 in a desired pattern. Then, an adhesive was coated on an exposed surface surrounding the fluid exothermic composition 2, and a covering material 3, as guided by a roller, was placed on the composition from above. The base material 1 and the covering material 3 were bonded together, with the fluid exothermic composition 2 sandwiched between them. Then, an adhesive layer 5 having a thickness of 50 $\mu$m was formed on an exposed surface of the base material 1. A continuous exothermic sheet thus obtained was extended about 7 mm by a roll press from the fluid exothermic composition 2 and was punched into a trapezoidal shape intended to cover the back of the toes.

Figure 2:
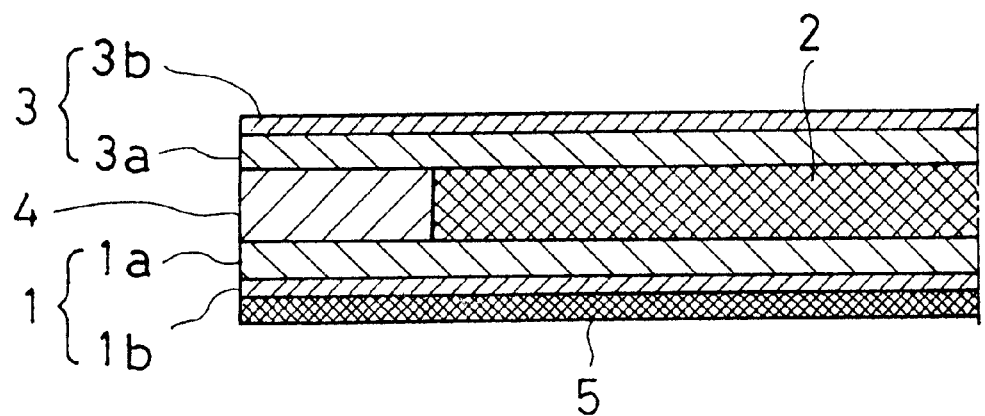
FIG. 2 is a schematic sectional view of the first embodiment of the invention.

As a schematic sectional view of FIG. 2 shows, the base material 1 is a laminate consisting of a water absorbable rayon nonwoven fabric 1a of about 80 g/m² and a gas impermeable and water impermeable polyethylene sheet 1b of about 50 μmm wide, with a fluid exothermic composition 2 printed on the nonwoven rayon fabric 1a of the base material 1 for direct contact therewith.

The covering material 3 is a laminate consisting of a water permeable rayon nonwoven fabric 3a of about 80 g/m² and a gas permeable polyethylene sheet 3b having a width of about 50μ, the laminate having a moisture permeability of 1000 g/m². The covering material 3 is so laminated as to allow the fluid exothermic composition 2 to come in direct contact with the rayon nonwoven fabric 3 of the covering material 3.

For the adhesive layer 5 an acrylic adhesive is used. In order to enhance the adhesion of the adhesive layer 5 to the base material 1, the exposed surface of the polyethylene sheet 1b of the base material 1 has been previously roughened by corona treatment to a wetting index of the order of 40 dyne or more.

The fluid exothermic composition 2 was prepared by blending 100 parts by weight of iron powder, a heat generating material (DKP manufactured by Dowa Teppun K, K,), 0.5 part by weight of water absorptive polymer (5000 MPS manufactured by Sanyo Kasei K. K.), 1.4 parts by weight of thickener (Celogen EP manufactured by Dauchi Kogyo Seiyaku K. K.), 8.6 parts by weight of activated carbon 5 (SA-SUPER manufactured by Norit), 4.3 parts by weight of sodium chloride as a metal chloride, and 0.3 part by weight of sodium polyphosphate as a pH adjustor, and adding excess water to the blend to provide a viscosity of 500,000 cps or so at a temperature of 20° C.

The word "viscosity" herein means a viscosity value measured by using a viscometer, type BH manufactured by Tokimec Inc., with a #7 rotor at a rotational speed of 2 rpm and a beaker having an inner diameter of 85 ømm, at a temperature of 20° C.

Therefore, the fluid exothermic composition contains excess water which functions as a barrier layer to prevent contact between the iron powder and air. As a result, it has been found that no or little, if any, exothermic reaction does occur.

When the fluid exothermic composition 2 is screen printed on the base material 1 to a thickness of 20 μm, the excess water in the exothermic composition begins to be absorbed by the water absorptive nonwoven rayon fabric 1a and, after the covering material 3 is placed, excess water is absorbed by the rayon nonwoven fabric 3a of the covering material 3 until the proportion of water in the exothermic composition 2 reaches the optimum condition for generation of the preset exothermic temperature.

However, whereas some time is required before the excess water is absorbed by the base material 1 and covering material 3 until the predetermined water content is reached, the time required after the fluid exothermic composition 2 is printed on the base material 1 and until the resulting foot warming exothermic device is enclosed in the gas impermeable pouch is zero point odds second at most, there being no possibility that the proportion of water in the fluid exothermic composition 2 reaches the optimum proportion for generation heat before the device is enclosed in the gas impermeable pouch.

Thus, there is no possibility of the fluid exothermic composition 2 generating heat before the foot warming exothermic device is enclosed in the gas impermeable pouch, nor is there any possibility that exothermic reaction products coagulate before such time, resulting various harms including, for example, decreased yield, handling difficulty, complex maintenance work with the manufacturing equipment, limitations imposed upon operating time of the manufacturing equipment or operator working hours, and difficult jobs involved in coagulated matter handling.

The excess water in the fluid exothermic composition 2 is absorbed by the water absorptive rayon nonwoven fabric 1a of the base material 1 and the water absorptive rayon nonwoven fabric 3a of the covering material 3 so that the proportion of the water will reach a suitable level for realizing a suitable proportion of water to obtain the predetermined exothermic temperature after the foot warming exothermic device is enclosed in the gas impermeable pouch and before it is delivered to the user through a distribution channel. Therefore, the exothermic composition 2 is not liable to quality deterioration before the gas impermeable pouch is broken to allow the content to be exposed to air, so that the exothermic composition 2 can be maintained in high quality. Moreover, an exothermic reaction starts immediately when the pouch is broken for removing the foot arming exothermic device, and the predetermined exothermic temperature is quickly reached.

Furthermore, the fluid exothermic composition 2 has high fluidity and can be laminated on the base material 1 by printing or coating. Therefore, in contrast to the case of the prior art in which an exothermic composition in powder form is simply placed on the base material 1, the fluid exothermic composition can be accurately laminated at high speed within the predetermined range and to a uniform thickness.

The foot warming exothermic device, enclosed in a gas impermeable pouch, was allowed to stand for 10 days. Thereafter, the pouch was broken to remove the foot warming exothermic device and then the device was applied by using an adhesive layer 5 directly to the back of a portion of the foot extending from the toes to the balls of the base of the toes. Good exothermic effect was obtained over more than 6 hours.

During this application of the foot warming exothermic device, it was found that by virtue of its ultra-thin formation the exothermic device was flexible as a whole so that it felt soft to the foot, readily deformed along a curved portion of the foot, conformed to the concave and convex configuration of the back of the toes, followed the movement of the sole of the foot very well through its deformation, and exhibited good contact capability relative to the site of application. No separation of the exothermic device from the site of application was observed and good warming effect was obtained. It was found that the device warmed the toes of the foot effectively from the back.

In such application, the adhesive layer 5 of the foot warming exothermic device can be applied directly to the back of the foot. Therefore, it is possible to effectively warm from the sole side over a range extending from the toe to the balls at the base of the toes.

Further, during such application, the exothermic composition 2 is not liable to movement, and distribution of the exothermic temperature of the foot warming exothermic device is uniform, there being no possibility of low temperature burn, which means higher safety in use.

The configuration of the foot warming exothermic device of the invention is not limited to that in the foregoing embodiment. For example, in the foot warming exothermic device representing the second embodiment of the invention shown in plan in FIG. 3, the fluid exothermic composition 2 (2a, 2b) is printed on a wrapper consisting of an inner sole cover-like base material 1 and a covering material 3 in such a way that a semi-elliptic portion extending from the toes of the foot to the toe root and a plantar arch portion are separately printed, and portions other than those for the fluid exothermic composition are adhesively joined.

In this case, though not shown, the device may be alternatively a foot warming exothermic device for toe use such that on the semi-elliptic base material is printed a fluid exothermic composition smaller than the base material but similar thereto, and a covering material of the same shape as the base material is placed on them from above and sealingly joined with them. Another alternative form may be a foot warming exothermic device for the plantar arch such that on a base material of a crescent shape is printed a fluid exothermic composition smaller than the base material but similar thereto in shape, and a covering material of the same shape as the base material is placed on them from above and sealingly joined with them.

Instead of the above form, though not shown, in a wrapper consisting of an inner sole cover-like base material 1 and a covering material 3, the fluid exothermic composition may be printed over a generally whole surface of the base material than the peripheral sealing edge portion so that the sole of the foot can be warmed almost all over.

Figure 4:
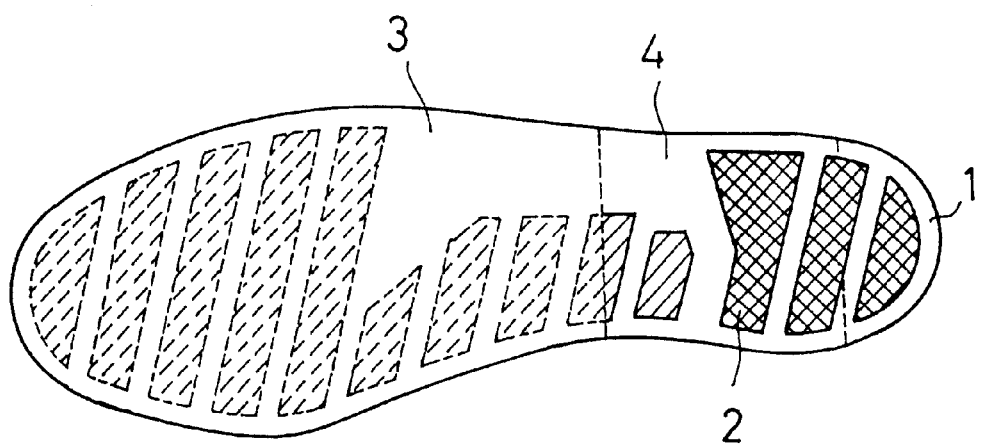
FIG. 4 is a plan view of a third embodiment of the invention.

The foot warming exothermic device representing a third embodiment of the invention shown in plan in FIG. 4 is such that in a wrapper consisting of an inner sole cover-like base material 1 and a covering material 3 the fluid exothermic composition 2 is printed in belt form over the entire surface of the sole portion excepting a side portion of the sole adjacent the plantar arch which contacts the ground. The portion other than the fluid exothermic composition 2 may be sealingly closed by adhesion. The foot warming exothermic device representing a fourth embodiment of the invention is such that the fluid exothermic composition 2 is printed on a front sole portion 2 (2a), a plantar arch and portion extended therefrom 2 (2b), and a heel portion 2 (2c). Portions other than the fluid exothermic composition may be sealingly closed by adhesion.

Figure 3:
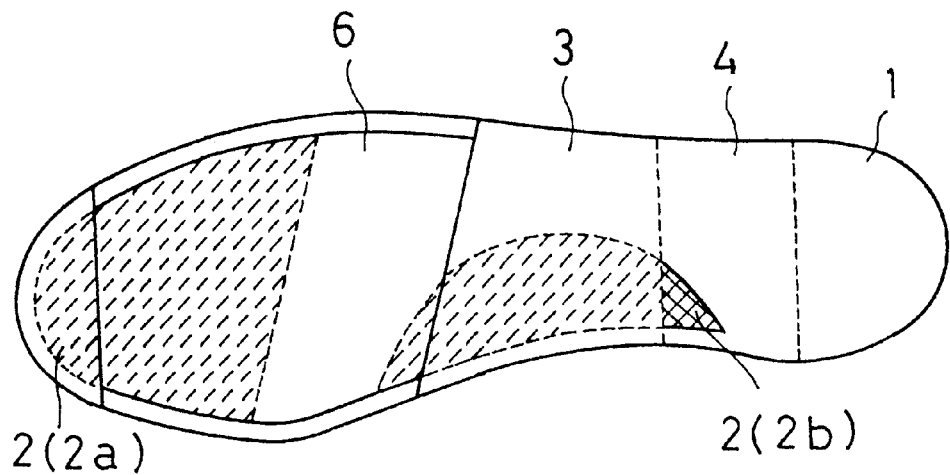
FIG. 3 is a plan view of a second embodiment of the invention.
Figure 5:
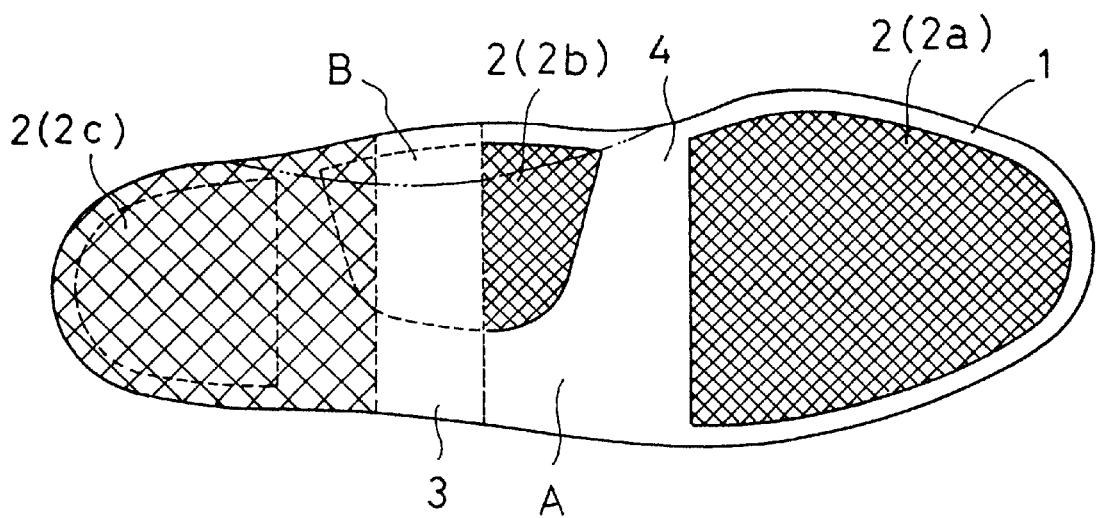
FIG. 5 is a plan view of a fourth embodiment of the invention.
Figure 6:
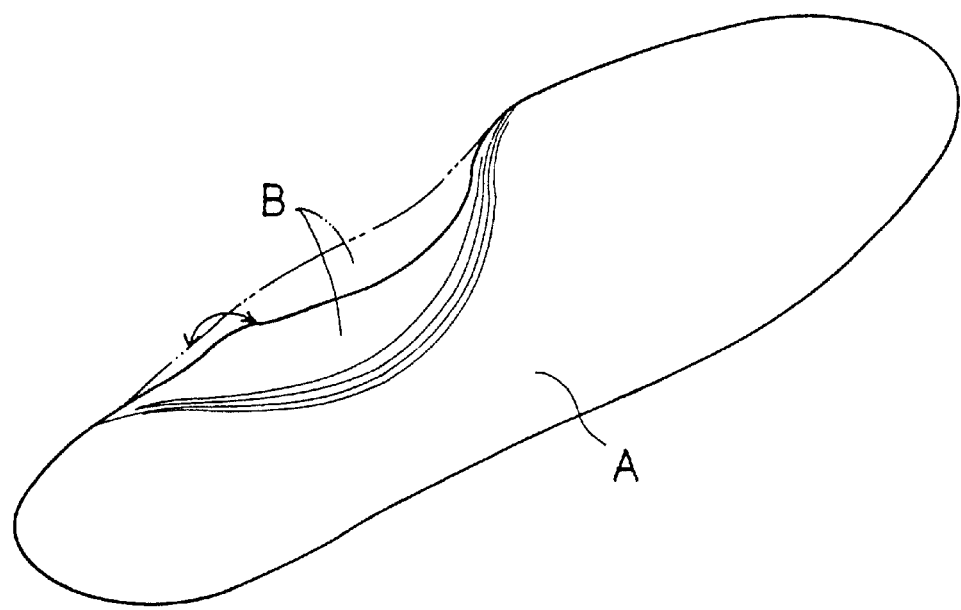
FIG. 6 is a perspective view of the fourth embodiment of the invention.

According to the first method of the invention, the foot warming exothermic device may be configured to cover any desired site. For example, the foot warming exothermic device may be formed into an inner cover type configuration as shown in FIG. 3 or 4, or may be formed into such a configuration that a portion of the peripheral edge portion of an inner sole cover pattern A, for example, a portion corresponding to the plantar arch is extended as shown in FIGS. 5 and 6 depicting the fourth embodiment.

Where the foot warming exothermic device is extended from a portion corresponding to the plantar arch in this way, with the fluid exothermic composition 2 disposed also in the extended portion in continuation to the plantar arch, when the foot warming exothermic device is placed in a shoe, or when it is applied to the sole of the foot, the foot pattern A and the portion B extended in continuation thereto can be deformed along a side of a portion of the foot including the plantar arch and a portion continued therefrom, so that the plantar arch and a portion extending therefrom to a side of the foot can be covered with the exothermic composition. Thus, a portion of the plantar arch at which a large number of pores concentrate can be effectively warmed by supplying warming heat to that portion from side and bottom, whereby good thermo-therapeutic effect can be obtained.

Figure 7:
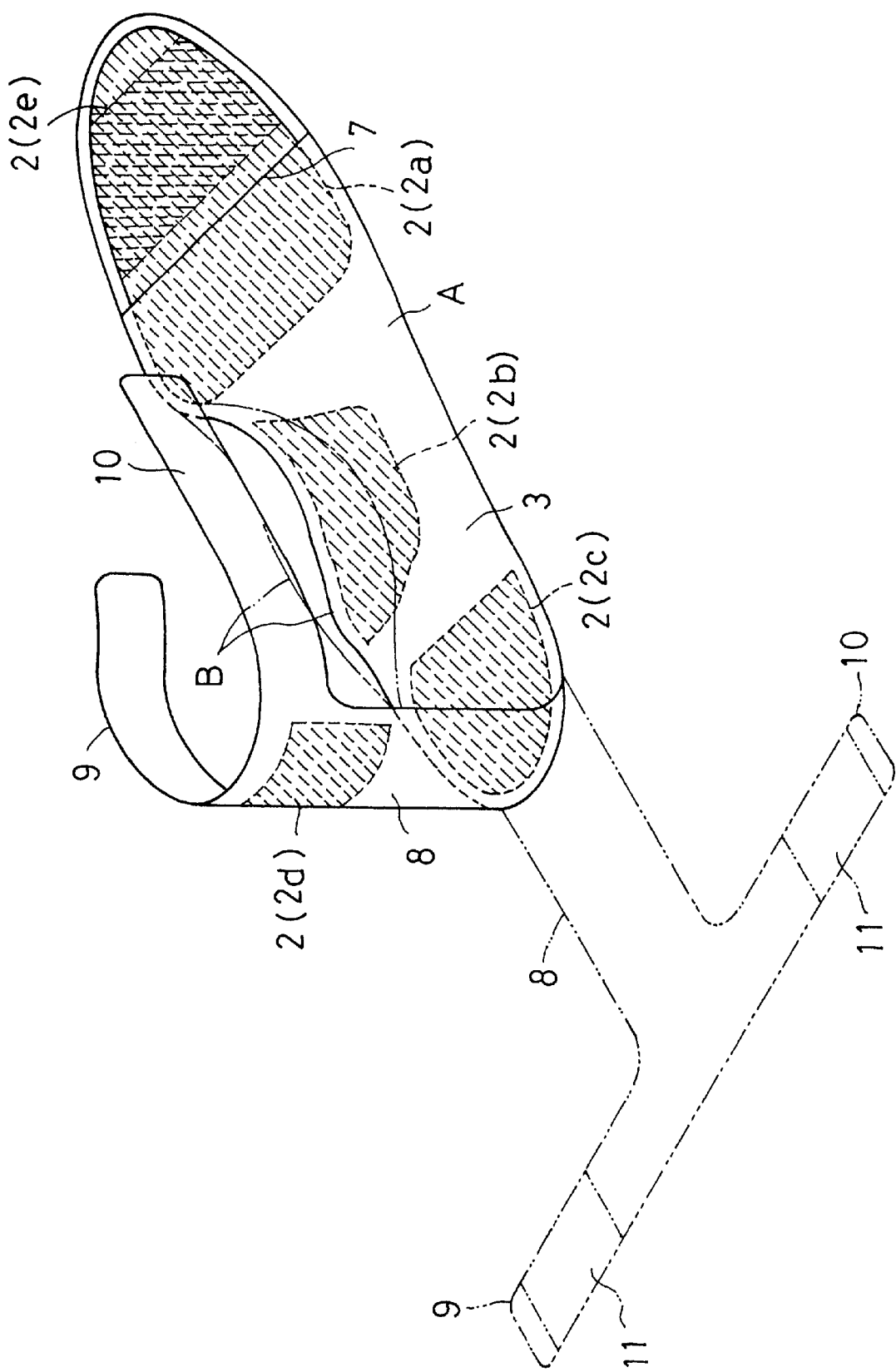
FIG. 7 is a perspective view of a fifth embodiment of the invention.
Figure 8:
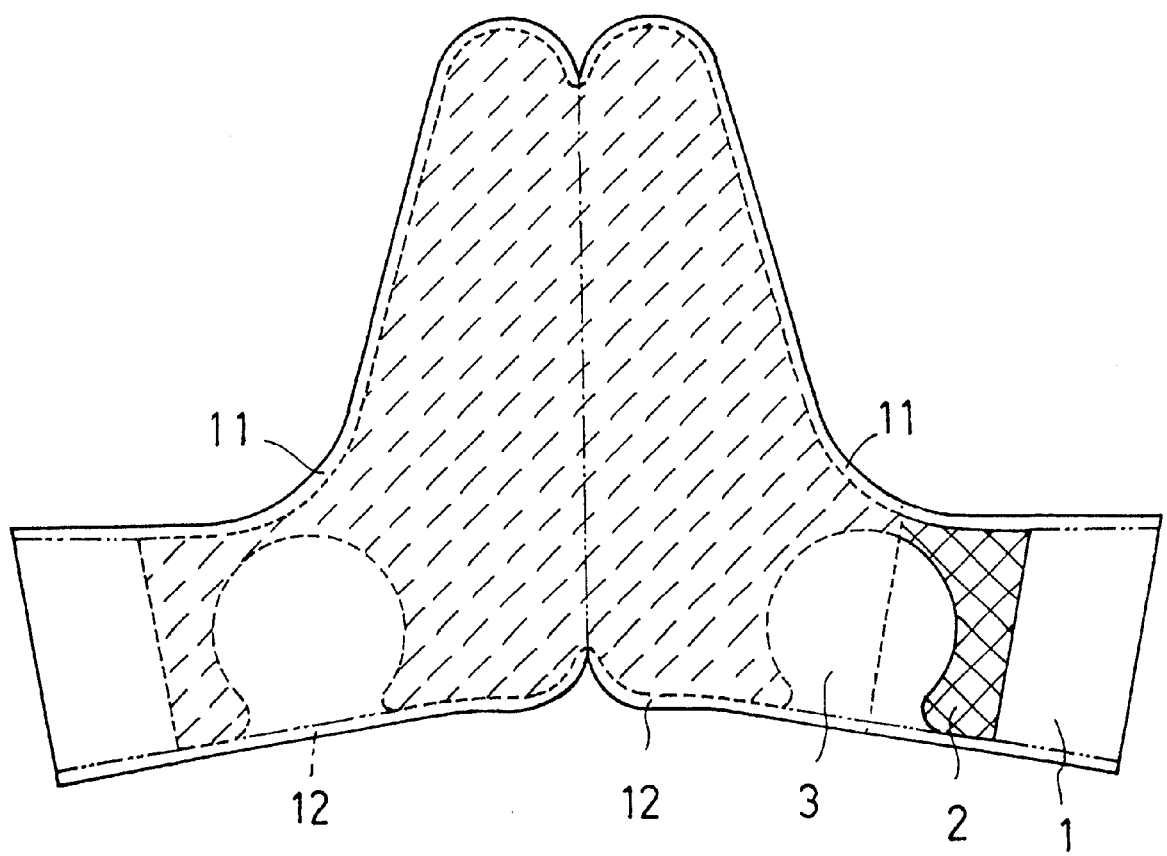
FIG. 8 is a development of a sixth embodiment of the invention.

In a fifth embodiment of the invention shown in perspective in FIG. 7, the device includes, in addition to the above arrangement, an instep front portion 7 covering the tip of the toe and the upper side of the base of the toes, a bulged portion 8 continued from the rear edge of a portion corresponding to the heel and extending to a position above the ankle portion, and adhesive portions 9,10 provided in continuation to both sides of the end of the bulged portion 8.

The fluid exothermic composition 2 (2a, 2b, 2c, 2d, 2e) comprises a horseshoe-like portion (2a) corresponding to the ball up to the toe, a portion (2b) corresponding to the plantar arch including a foot pattern portion A and bulge B, a portion (2c) corresponding to the heel, a portion (2d) corresponding to a rear upper portion of the ankle, and a portion (2e) above the toes, these portions being separately disposed.

This foot warming exothermic device is suitably applicable to sandals and may be used just as in putting on a sandal, with the toe inserted between the instep front portion 7 and the foot pattern portion A, that is, the toe inserted between the horseshoe-like portion (2a corresponding to the ball up to the toe and the portion (2e) above the toes, with the adhesive is portions 9 and 10 applied to the upper side of the ankle.

The exothermic composition (2a) disposed at the horseshoe-like portion corresponding to the ball up to the toe and the exothermic composition (2e) disposed at the portion above the toes warm, from above and from below, a site of from the toe to the ball at the toe root, and the exothermic composition (2b) disposed at the portion corresponding to the plantar arch including foot pattern portion A and bulge B well conforms to the concave and convex configuration of the plantar arch to efficiently warm the plantar arch. The exothermic composition (2c) disposed at the site corresponding to the heel warms the heel from below and the exothermic composition (2c) disposed at the portion corresponding to the upper rear side of the ankle warms Achilles' tendon and its vicinity.

The exothermic composition (2c) disposed at a site corresponding to the upper rear side of the ankle contains a compress medication to provide a therapeutic compress effect for treatment of achillodynia.

In a sixth embodiment of the invention shown in FIG. development view, a wrapper consisting of base material 1 and covering material 3 divides a sock into symmetrical parts, right and left, which parts are held in continuation centrally of the sole of the sock.

That is, on a raw fabric for base material 1 comprised of a water absorptive and gas permeable, stretchable nonwoven fabric (40 g/m$^2$ thick)/porous film (10 $\mu$m thick) polyester nonwoven fabric (60 g/m$^2$ thick, impregnated with 10 g/m$^2$ of CMC) is printed as a fluid exothermic composition 2 in divisions to a predetermined pattern. On these is placed a raw fabric for covering material 3 consisting of a water absorptive and gas permeable, stretchable nonwoven fabric (40 g/m$^2$ thick)/porous film (40 $\mu$m)/polyester nonwoven fabric (60 g/m$^2$ thick, impregnated with 10 g/m$^2$ of CMC). Peripheral edge portions of the base material 1 and the covering material 3 are cut by fusion.

In this case, the peripheral edges of the base material 1 and the covering material 3 are sealingly joined, and the base material 1 and the covering material 3 are bonded together with the fluid exothermic composition 2. Thus, any outward leak of the fluid exothermic composition or movement of the exothermic composition between the base material 1 and the covering material 3 during use of the device is prevented. Any abrasive contact at the portion corresponding to the ankle may give a disagreeable feel and, therefore, the fluid exothermic composition 2 is disposed at portions other than the ankle portion.

Then, a foot warming exothermic device obtained by fusion cutting is folded in the center of a sock, which may be used in such a way as to enclose the edge 11 extending from the toe through the instep to the ankle and the edge 12 extending from the heel to the ankle, for example, in a boot.

With the foot warming exothermic device of this embodiment, back side, instep side, and side portions extending from the upper side of the ankle to the toe are totally warmed, except the ankle joint portion. Since the foamed polyethylene sheet of the covering material 3 contacts the skin of the foot, flexibility of the device is enhanced to give a comfortable feel to the skin.

Figure 9:
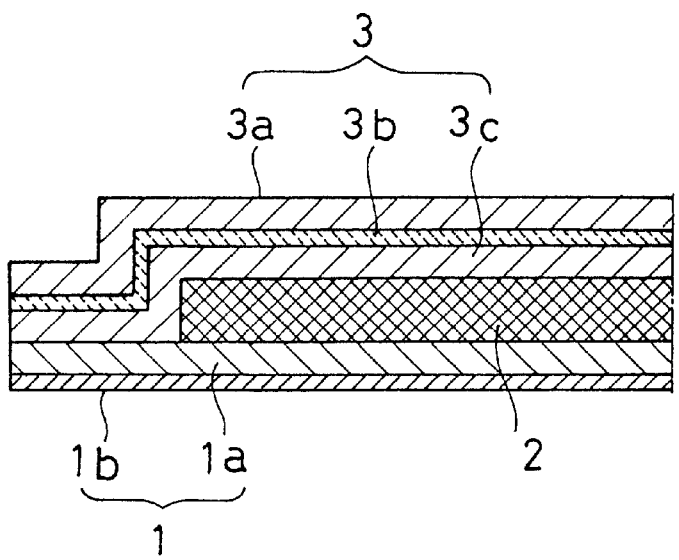
FIG. 9 is a schematic view in section of a seventh embodiment of the invention.
Figure 10:
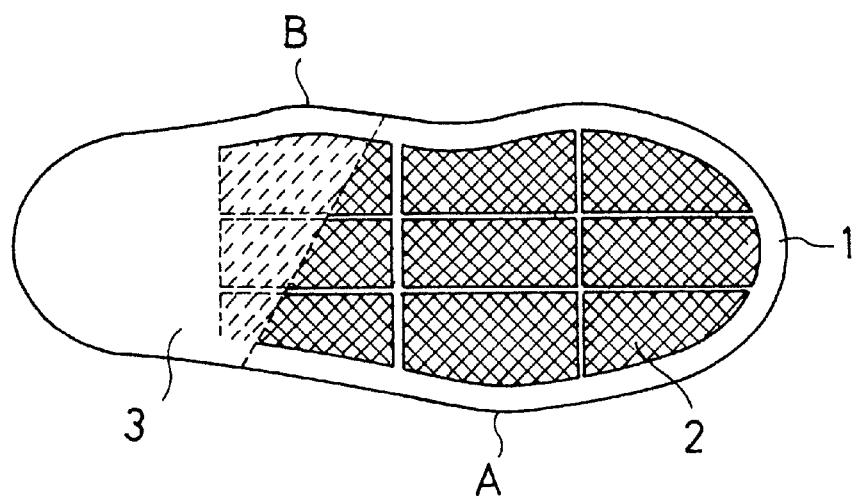
FIG. 10 is a plan view of the seventh embodiment of the invention.

In the foot warming exothermic device representing a seventh embodiment of the invention shown in fragmentary section in FIG. 9 and in plan in FIG. 10, a card board for insertion between the base material 1 and the covering material 3 is omitted. The fluid exothermic composition is screen printed on the base material 1, and then the covering material 3 is placed on the base material and fluid exothermic composition from above, at which time adhesion bonding is effected to join the entire portions around the fluid exothermic composition 2. Simultaneously, the joined portions are punched out to the predetermined shape.

In this embodiment, the covering material 3 comprises an outer layer consisting of a polypropylene nonwoven fabric (Type 2030, manufactured by Idemitsu; weight per unit area 30 g/m$^2$) 3a, and a porous film (Espoire, manufactured by Mitsi Toatsu K. K., moisture permeability 4000 g/m hr), and an inner layer formed of cardboard K liner (NS liner, manufactured by Nihon Shigyo, weight per unit area 200 g/m$^2$ water absorption 114 g/m$^2$) 3c, which components are laminated through the intermediary of an adhesive made by melt blow (Type 5Q543, manufactured by NSC). A quantity of this adhesive used is 5 g/m$^2$ between nonwoven fabric 3a and porous film 3b; and 30 g/m$^2$ between porous film 3b and cardboard K liner 3c.

In this embodiment, as FIG. 10 shows, a printing pattern of the fluid exothermic composition 2 is formed over the whole sole portion, except the heel portion, the sole portion being divided by lattice-like non-printed portions into plural regions. In these lattice-like non-printed portions, outer edge portions are bonded simultaneously when the base material 1 and the covering material 3 are bonded together. In this embodiment, therefore, movement of exothermic composition 2 beyond respective region is more positively prevented and the flexibility of the device as a whole is very noticeably enhanced.

In this embodiment, the device as a whole has an inner sole cover configuration. Therefore, no adhesive layer 5 is provided, in which point the embodiment is different from Example 1.

With the exception of the above noted point in which this embodiment is different from the Example 1, other aspects of the construction of this embodiment are the same as those of Example 1, including the composition of the thin exothermic composition and the thickness thereof.

This foot warming exothermic device was enclosed in a gas tight pouch and the same was allowed to stand for 30 days. Thereafter, the gas tight pouch was broken to remove the foot warming exothermic device. The device, placed in a shoe for use. Good warming effect was obtained over a period of 7.5 hours.

Figure 11:
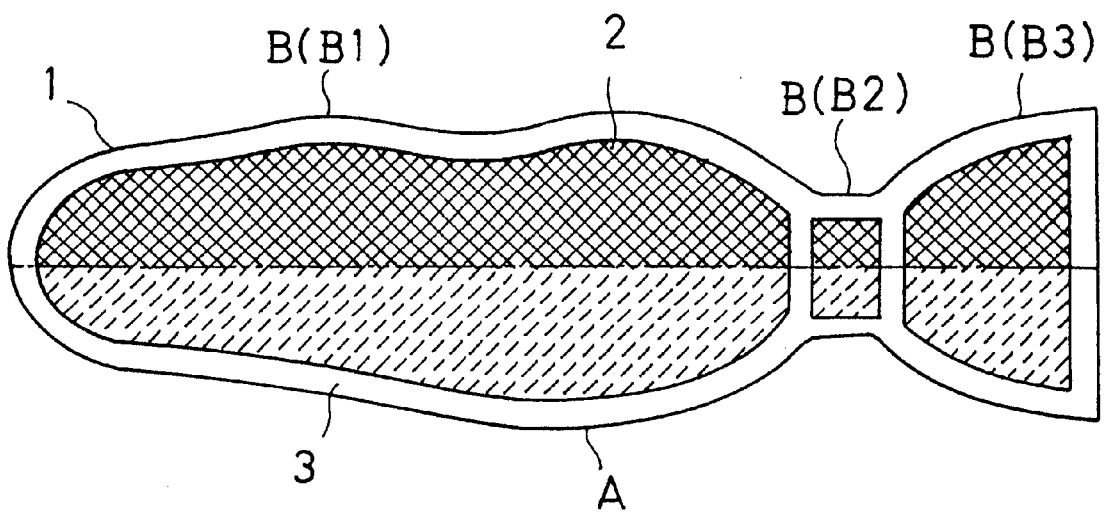
FIG. 11 is a plan view of an eighth embodiment of the invention.
Figure 12:
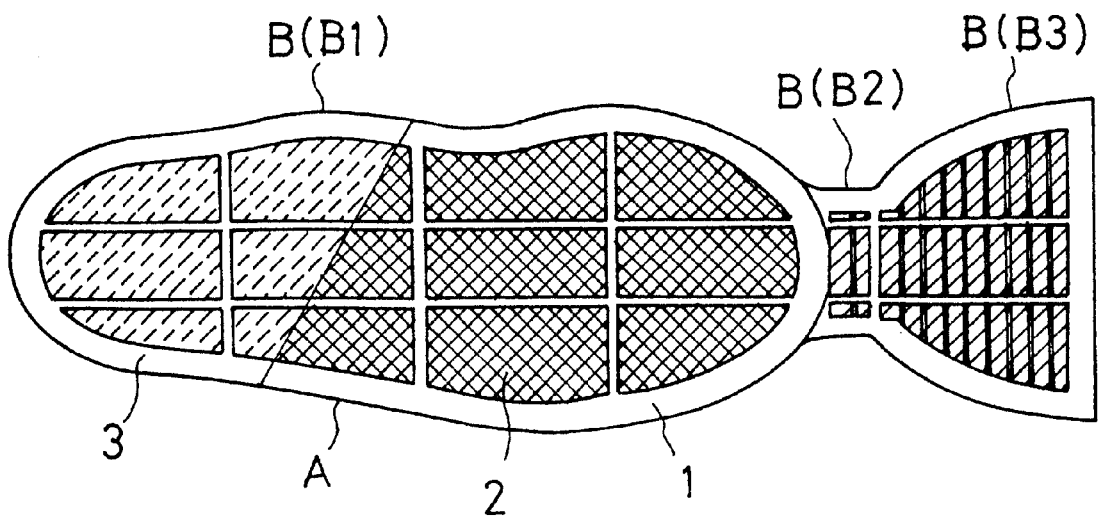
FIG. 12 is a plan view of a ninth embodiment of the invention.
Figure 13:
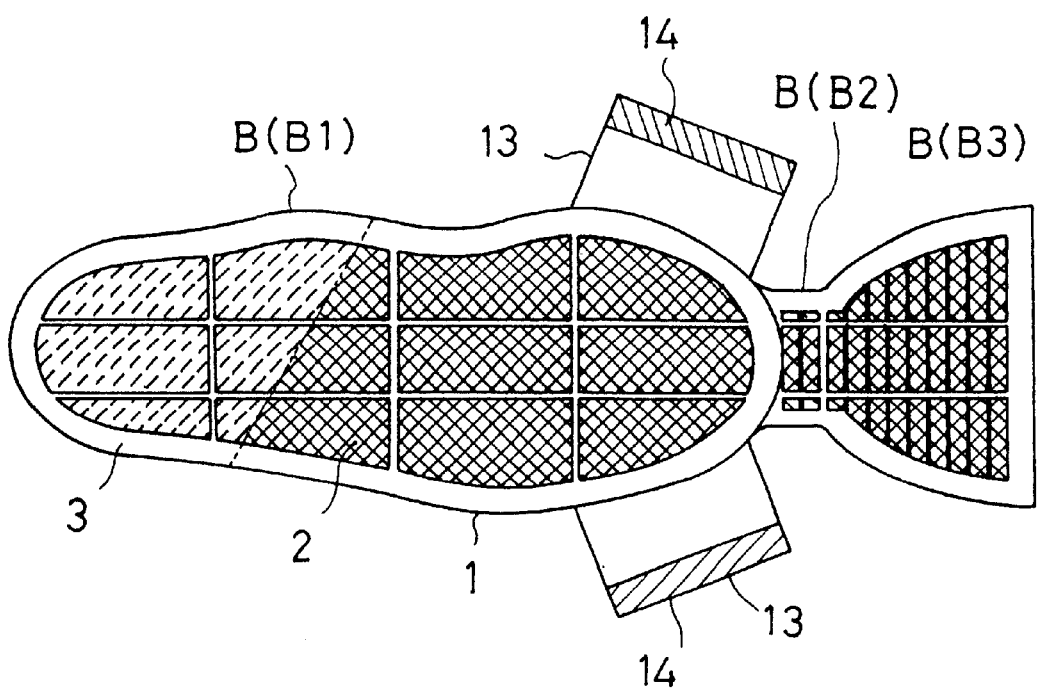
FIG. 13 is a plan view of a tenth embodiment of the invention.

The foot warming exothermic device representing an eighth embodiment of the invention shown in plan in FIG. 11, the foot warming exothermic device representing a ninth embodiment of the invention shown in plan in FIG. 12, and the foot warming exothermic device representing a tenth embodiment of the invention shown in FIG. 13 include, in addition to a bulged portion B(B1) continued to a plantar arch portion of a foot pattern portion A, a bulged portion B(B2) covering the front end of the toe from the toe end portion, and a bulged portion B(B3) covering the instep of the foot from the toe in continuation to the bulged portion B(B2), and have the fluid exothermic composition 2 disposed all over therein with the exception of a portion between the toe and the bulged portion B(B2) which is to be bent slightly when in use and a portion connecting between two bulged portions B(B2, B3) of the toe.

In the foot warming exothermic device representing a ninth embodiment of the invention shown in FIG. 12, and the foot warming exothermic device representing a tenth embodiment of the invention shown FIG. 13, bulged portion B (B2, B3) on the toe side which corresponds to a site at which toe movement is particularly active has the thin exothermic composition 2 disposed therein in divided lots so that the movement of exothermic composition in that portion is prevented in a more positive and refined manner.

With any of these foot warming exothermic devices, in use, by simply folding the bulged portion B(B2, B3) from the toe onto the instep it is possible to warm the toe portion from three directions, namely, from the sole side, the toe side, and the instep side.

In the case of the foot warming exothermic device representing the ninth embodiment of the invention shown FIG. 12, as well as the foot warming exothermic device representing the tenth embodiment of the invention shown in FIG. 13, the fluid exothermic composition 2 is printed part by part in plural regions so that the exothermic composition and/or exothermic reaction products can be more positively prevented.

In the case of the foot warming exothermic device representing the tenth embodiment of the invention shown in FIG. 13, stop belts 13 extend from both ends of the front portion of the foot, with an adhesive portion 14 laminated at the front end of the stop belt 13.

Figure 14:
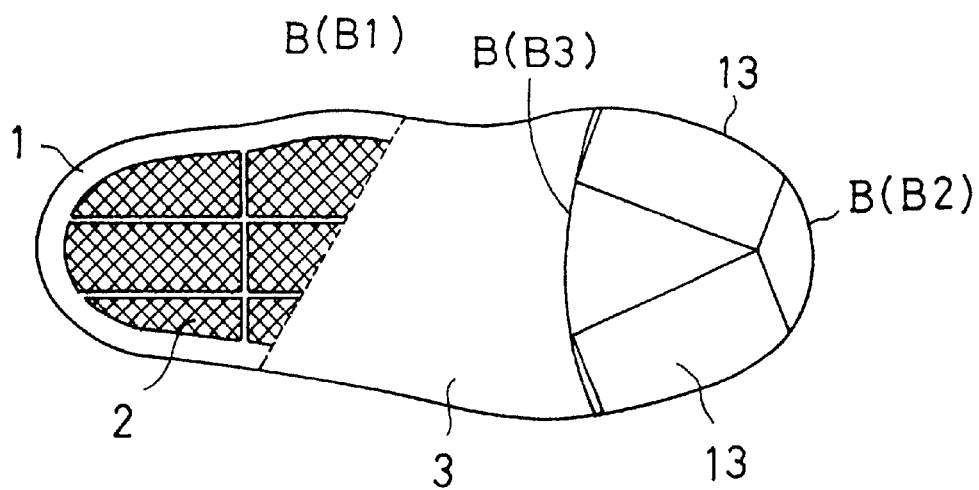
FIG. 14 is a plan view of the tenth embodiment when in use.

In use, as FIG. 14 shows in plan, both stop belts 13 are placed over the bulged portion B (B3) folded over the instep, and the adhesive layer 14 is placed on the bulged portion B(B3) for adhesion therewith, whereby the device is formed into a slipper-like shape.

The foot warming exothermic devices of a complex configuration of the foregoing embodiments use a fluid exothermic composition in particular as necessary an exothermic composition, and because of this fact it is possible to laminate the fluid exothermic composition by printing or the like on the base material to a desired pattern, which has been impossible in the prior art.

Not shown, though, over the entire surface of a cardboard core of 180 g/m$^2$, as a base material, was printed a fluid exothermic composition similar to the one used in Example 1 to the thickness of 820 $\mu$m, and on top of them was placed a cardboard core of 180 g/m$^2$ of a similar type, as a covering material, by passing the same through lap rolls so that the base material and the covering material were joined together by virtue of the viscosity of the fluid exothermic composition. Thus, a continuous exothermic sheet was produced. Then, by using a roll press the continuous exothermic sheet was continuously punched into an inner sole cover-like shape. Then, the resulting foot warming exothermic device was interposed between a laminated thin sheet formed of 40 $\mu$m polyethylene film/12 $\mu$m polyester thin sheet and a laminated thin sheet (moisture permeability 850 g/m$_2$)

formed of 40 µm polyethylene porous thin sheet/30 g/m² polypropylene nonwoven fabric. The laminate was punched to a size of about 7 mm larger over its entire periphery than the foot warming exothermic device and was heat sealed at the same time, whereby a foot warming exothermic device was obtained.

Then, the foot warming exothermic device was enclosed in a gas impermeable pouch and was allowed to stand one day. Then, the gas impermeable pouch was broken for use. Good exothermic effect was obtained.

In this case, the base material and the covering material are inexpensive and the two films can be sealingly joined by heat sealing. This enables continuous production of the foot warming exothermic device.

Further, since the base material and the covering material are bonded together by means of the viscosity of the fluid exothermic composition, the exothermic sheet can be easily produced at low cost.

Furthermore, since the exothermic device is packed in such a condition that it is sandwiched between gas permeable cardboard cores without adhesion, air is easily allowed to flow toward both surface and back sides during the walk of the user, and accordingly a contact area between the exothermic device and water is present on both surface and back sides. Therefore, reaction efficiency is enhanced even in the case of one side air permeation.

What is claimed is:

1. An exothermic foot warming device comprising a sheet of base material, an exothermic composition in viscous fluid form, said exothermic composition containing an amount of water effective to provide a viscosity of the composition within the range of about 50,000 to about 6,500,000 cps at 20° C. and to form a barrier layer for blocking oxygen when the viscous fluid exothermic composition is applied to a predetermined area of said sheet base material, and a covering material covering said viscous fluid exothermic composition, at least a part of at least one of said base sheet material or said covering material being gas permeable.

2. A foot warming exothermic device as set forth in claim 1, in which said exothermic device is configured to cover a whole area of a sole of a human foot.

3. A foot warming exothermic device as set forth in claim 1, in which said exothermic device is configured to cover at least that part of a sole of a human foot comprising toes, instep and/or heel of the foot.

4. The foot warming device defined in claim 1, wherein said covering material comprises a water absorbable sheet material.

5. The foot warming device defined in claim 1, further comprising a layer of water absorbable material on said sheet base material, said viscous fluid exothermic composition being applied to said layer of water absorbing material.

6. The foot warming device defined in claim 1, wherein said viscous fluid exothermic composition acts as an adhesive bonding said sheet base material and said covering material.

* * * * *